(12) United States Patent
Magnin et al.

(10) Patent No.: US 7,612,773 B2
(45) Date of Patent: Nov. 3, 2009

(54) APPARATUS AND METHOD FOR RENDERING FOR DISPLAY FORWARD-LOOKING IMAGE DATA

(76) Inventors: Paul A. Magnin, 23 Greybirch Rd., Andover, MA (US) 01810; John W. Goodnow, 8 Radcliffe Rd., Arlington, MA (US) 02474; Russell W. Bowden, 2 Joyce Dr., Tyngsboro, MA (US) 01879; Graham A. Wright, 34 Albemarle Ave., Toronto, ON (CA); Alexander J. Dick, 187 Hudson Dr., Toronto, ON (CA) M4K 1H7; Perry Radau, 428-155 Dalhousie St., Toronto, ON (CA); John J. Graham, Apartment 1006, 77 St. Clare Ave. East, Toronto, ON (CA) M4T 1M5

( * ) Notice: Subject to any disclaimer, the term of this patent is extended or adjusted under 35 U.S.C. 154(b) by 310 days.

(21) Appl. No.: 11/437,687

(22) Filed: May 22, 2006

(65) Prior Publication Data

US 2007/0268287 A1    Nov. 22, 2007

(51) Int. Cl.
*G06T 15/00* (2006.01)
(52) U.S. Cl. .................... 345/419; 345/424; 362/19; 600/437; 600/443; 600/462
(58) Field of Classification Search ........... 345/419, 345/424; 600/437, 443, 445, 462, 463; 362/19
See application file for complete search history.

(56) References Cited

U.S. PATENT DOCUMENTS

| | | | |
|---|---|---|---|
| 3,542,014 A | 11/1970 | Peronneau | |
| 3,779,234 A | 12/1973 | Eggleton et al. | |
| 3,817,089 A | 6/1974 | Eggleton et al. | |
| 3,827,115 A | 8/1974 | Bom | |
| 3,938,502 A | 2/1976 | Bom | |
| 4,316,390 A | 2/1982 | Kretz | |
| 4,391,282 A | 7/1983 | Ando et al. | |
| 4,408,612 A | 10/1983 | Utsugi | |
| 4,489,728 A | 12/1984 | Matsuo et al. | |

(Continued)

OTHER PUBLICATIONS

Slager et al., "Vaporization of Atherosclerotic Plaque by Spark Erosion", JACC, Jun. 1985, 5:00. 1382-1386-6.

(Continued)

*Primary Examiner*—Phu K Nguyen
(74) *Attorney, Agent, or Firm*—Leydig, Voit & Mayer Ltd

(57) ABSTRACT

An apparatus and method for rendering for display forward-looking image data. The apparatus includes rendering for display image data from a forward-looking conical section of tissue collected by an image data collection device, comprising a data input unit configured to receive the image data; and an image data processing unit configured to rasterize the image data onto a projected three-dimensional geometric model to produce a rasterized image, thereby giving the appearance of three-dimensions when displayed. The method includes a method of rendering for display image data from a forward-looking conical section of tissue collected by an image data collecting device, comprising receiving the image data; and rasterizing the image data onto a projected three-dimensional geometric model to produce a rasterized image, thereby giving the appearance of three dimensions when displayed.

78 Claims, 7 Drawing Sheets
(1 of 7 Drawing Sheet(s) Filed in Color)

U.S. PATENT DOCUMENTS

| | | | |
|---|---|---|---|
| 4,587,972 A | 5/1986 | Morantte, Jr. | |
| 4,794,931 A | 1/1989 | Yock | |
| 4,805,155 A | 2/1989 | Shiraishi et al. | |
| 4,841,977 A | 6/1989 | Griffith et al. | |
| 4,899,757 A | 2/1990 | Pope, Jr. et al. | |
| 4,911,170 A | 3/1990 | Thomas, III et al. | |
| 4,917,097 A | 4/1990 | Proudian et al. | |
| 4,951,677 A | 8/1990 | Crowley et al. | |
| 5,000,185 A | 3/1991 | Yock | |
| 5,054,492 A * | 10/1991 | Scribner et al. | 600/463 |
| 5,115,814 A | 5/1992 | Griffith et al. | |
| 5,127,409 A * | 7/1992 | Daigle | 600/443 |
| 5,131,397 A | 7/1992 | Crowley | |
| 5,176,141 A | 1/1993 | Bom et al. | |
| 5,186,177 A | 2/1993 | O'Donnell et al. | |
| 5,203,338 A | 4/1993 | Jang | |
| 5,240,003 A | 8/1993 | Lancee et al. | |
| 5,243,988 A | 9/1993 | Sieben et al. | |
| 5,271,400 A | 12/1993 | Dumoulin et al. | |
| 5,271,402 A * | 12/1993 | Yeung et al. | 600/437 |
| 5,284,148 A | 2/1994 | Dias et al. | |
| 5,313,949 A | 5/1994 | Yock | |
| 5,321,501 A | 6/1994 | Swanson et al. | |
| 5,345,940 A | 9/1994 | Seward et al. | |
| 5,353,798 A * | 10/1994 | Sieben | 600/462 |
| 5,361,768 A | 11/1994 | Webler et al. | |
| 5,368,035 A | 11/1994 | Hamm et al. | |
| 5,373,845 A * | 12/1994 | Gardineer et al. | 600/445 |
| 5,373,849 A | 12/1994 | Maroney et al. | |
| 5,375,602 A | 12/1994 | Lancee et al. | |
| 5,377,685 A | 1/1995 | Kazi et al. | |
| 5,379,772 A | 1/1995 | Imran | |
| 5,439,000 A | 8/1995 | Gunderson et al. | |
| 5,469,853 A | 11/1995 | Law et al. | |
| 5,485,845 A | 1/1996 | Verdonk et al. | |
| 5,588,432 A | 12/1996 | Crowley | |
| 5,594,842 A * | 1/1997 | Kaufman et al. | 345/424 |
| 5,606,454 A | 2/1997 | Williams et al. | |
| 5,651,366 A | 7/1997 | Liang et al. | |
| 5,699,806 A | 12/1997 | Webb et al. | |
| 5,921,934 A | 7/1999 | Teo | |
| 6,066,096 A | 5/2000 | Smith et al. | |
| 6,095,981 A | 8/2000 | McGahan | |
| 6,120,455 A | 9/2000 | Teo | |
| 6,267,727 B1 | 7/2001 | Teo | |
| 6,445,939 B1 | 9/2002 | Swanson et al. | |
| 6,450,964 B1 | 9/2002 | Webler | |
| 6,457,365 B1 | 10/2002 | Stephens et al. | |
| 6,780,157 B2 | 8/2004 | Stephens et al. | |
| 6,860,855 B2 | 3/2005 | Shelby et al. | |
| 6,863,676 B2 | 3/2005 | Lee et al. | |
| 6,960,172 B2 | 11/2005 | McGurkin et al. | |
| 7,022,082 B2 | 4/2006 | Sonek et al. | |
| 7,025,765 B2 | 4/2006 | Balbierz et al. | |
| 2002/0032437 A1 | 3/2002 | Andrews et al. | |
| 2002/0183826 A1 | 12/2002 | Dorn et al. | |
| 2003/0125757 A1 | 7/2003 | Patel et al. | |
| 2004/0113909 A1* | 6/2004 | Fenney et al. | 345/419 |
| 2005/0107688 A1 | 5/2005 | Strommer | |
| 2005/0128730 A1* | 6/2005 | Shindoh | 362/19 |

OTHER PUBLICATIONS

Slager, et al., "Spark Erosion and Its Combination with Sensing Devices for Ablation of Vascular Lesions", Chapter 13, in John H.K. Vogel and Spencer B. Kin, Ill, Interventional Cardiology: Future Directions, The C.V. Mosby Company, St. Louis, 1989, pp. 163-169. Presented Sep. 26, 1987 Santa Barbara.

Bom at al., "Intra-Arterial Ultrasonic Imaging for Recanalization by Spark Erosion," Ultrasound in Med. & Biol., vol. 14, No. 4, pp. 257-261, 1988.

Bom et al., "Early and Recent Interluminal Ultrasound Devices" International Journal of Cardiac Imaging 4:79-88, 1989, 1989 Kluwer Academic Publishers, Printed in the Netheralnds.

Harm ten Hoff et al., "Imaging artifacts in mechanically driven ultrasound catheters" 1989, vol. 4, pp. 195-199, International Journal of Cardiac Imaging.

Kimura at al., "Can Intravascular Ultrasound Yield Accurate Measuremetns of Vascular Anatomy? Documentation of the Critical Improtance of Uniform Rotational Velocity" 1994, vo. 1A(484) p. 173A, JACC.

Slager et al., "Removal of Cardiovascular Obstructions by Spark Erosion," public presentation of dissertation Dec. 17, 1997 at 3:45 PM, later printed in "Spark Erosion Under Ultrasound Guidance," Ch. 8, pp. 81-90, ICG Printing Dordrecht.

Evans et al., "Arterial Imaging with a New Forward-Viewing Intravascular Ultrasound Catheter, I, Initial Studies," Circulation, vol. 89, No. 2, pp. 712-717, Feb. 1994.

Ng et. al., "Arterial Imaging With a New Forward-Viewing Intravascular Ultrasound Catheter, II, Three-Dimensional Reconstruction and Display of Data," Circulation, vol. 89, No. 2, pp. 718-723, Feb. 1994.

Liang, D.H., "A Forward-Viewing Intravascular Ultrasound Catheter Suitable for Intracoronary Use," Biomedical Instrumentation & Technology, Jan./Feb. 1997. pp. 45-53.

Von Birgelen C., et. al., "Preintervention Lesion Remodeling affects Operative Mechanisms of Balloon Optimized Directional Coronary Atherectomy Procedures: a volumetric study with three dimensional intravascular ultrasound", Heart 2000; vol. 83, pp. 192-197.

Wolfram Research, "Mathworld: Rodrigues' Rotation Formula," http://mathworld.wolfram.com/RodriguesRotationFormula.html, May 1, 2006, pp. 1-2.

Catmull, E., "A Subdivision Algorithm for Computer Display of Curved Surfaces," Ph.D. Thesis, Report UTEC-CSc-74-133, Computer Science Department, University of Utah, Salt Lake City, UT, Dec. 1974. Also in "Computer Display of Curved Surfaces," Proc. IEEE Conf. on Computer Graphics, Pattern Recognition and Data Structures, May 1975.

Blinn,. J.F., and M.E. Newell, "Texture and Reflection in Computer Generated Images," Communications of the ACM, 19(10), Oct. 1976, pp. 542-547.

Heckbert, P.S., "Survey of Texture Mapping," IEEE Computer Graphics and Applications, 6(11), Nov. 1986, pp. 56-67.

Feldman, Mark, "The PC Game Programmer's Encyclopedia: Texture Mapping," http://www.geocities.com/SiliconValley/2151/tmap.html, Jun. 6, 2008; pp. 1-2.

Research Laboratory of Electronics at MIT Optical Devices—Laser Medicine and Medical Imaging Group, Progress Report 143, Chapter 11, 2000.

Research Laboratory of Electronics at MIT—Photonic Materials, Devices and Systems—Laser Medicine and Medical Imaging Group, Progress Report 144, Chapter 27, 2001.

* cited by examiner

| Index (n) | Angle (θ) | ImageData [n, 0..SamplesPerLine-1] |
|---|---|---|
| 0 | 0 * Δ Angle | ImageData [0, 0..SamplesPerLine-1] |
| 1 | 1 * Δ Angle | ImageData [1, 0..SamplesPerLine-1] |
| 2 | 2 * Δ Angle | ImageData [2, 0..SamplesPerLine-1] |
| 3 | 3 * Δ Angle | ImageData [3, 0..SamplesPerLine-1] |
| n | n * Δ Angle | ImageData [n, 0..SamplesPerLine-1] |
| ... | ... | ... |
| ... | ... | ... |
| ... | ... | ... |
| LinesPerFrame-1 | (LinesPerFrame-1) * Δ Angle | ImageData [LinesPerFrame-1, t], where t=0..SamplesPerLine-1 |

APPARATUS AND METHOD FOR RENDERING FOR DISPLAY FORWARD-LOOKING IMAGE DATA

BACKGROUND OF THE INVENTION

1. Field of the Invention

The invention is directed to an apparatus and method for rendering for display forward-looking image data.

2. Background of the Related Art

In the field of Interventional Medicine, catheters, laparoscopes, and endoscopes are frequently used to create images of tissues. These images can be used, for example, to diagnose and treat disease. Further, it may be advantageous in certain cases to employ medical images to guide and/or monitor progress during therapeutic treatment of a medical condition. Ultrasonic imaging and Optical Coherence Tomography (OCT) are imaging techniques that are well suited for such applications. For example, they can produce tomographic images in real-time from the end of, for example, a catheter, endoscope, or laparoscope. Images from these modalities tend to be displayed in planar tomographic formats. For example, when a mechanically or manually steered device is employed to rotate a transducer, the images are usually displayed as circular images. Although most medical Ultrasound and OCT images are scanned by mechanical rotation of the transducer, they can also be electronically scanned by steering the ultrasonic or optical beam from the end of the catheter or other device. New devices now incorporate manually rotated IntraVascular UltraSonic (IVUS) imaging.

When using, for example, a catheter, endoscope, or laparoscope in the confines of a vessel or body cavity for guiding and monitoring therapies, one frequently would like to visualize what lies ahead of the catheter, endoscope, or laparoscope tip. This is especially true when the therapeutic device is located on a distal most end of the catheter, endoscope, or laparoscope. Forward visualization can also be beneficial when one wishes to collect biopsy specimens from specific tissues in a minimally invasive fashion. Mechanically steered ultrasound and OCT devices are excellent at making images that are substantially perpendicular to an axis of the catheter, endoscope or laparoscope. However, for the purpose of guiding therapy, in some applications, it is preferable to have, for example, a transducer or optical fiber sweep out a conical forward-looking surface that depicts tissue that lies distal to a tip of the catheter, endoscope, or laparoscope.

The field of Interventional Medicine arose to apply less invasive technologies to the treatment of disease. For diagnostic and therapeutic guidance tools, Cardiovascular Interventionalists had fluoroscopy systems that allowed them to image the blood pool by injecting a radio-opaque contrast dye into the blood stream and then use a real time x-ray imaging technique to watch as that contrast dye passed through the vascular tree. A major limitation with this technology was that the fluoroscope did not, in fact, image the vessel tissue but rather the blood pool inside the vessel lumen. In an attempt to obtain an image of the vessel wall and not just the blood pool, ultrasonic imaging transducers were mounted at the distal end of catheters and positioned in the arteries. These transducers were typically mounted on catheters that were approximately 1 mm in diameter. The ultrasonic transducers typically had apertures of about 65 mm-0.75 mm. This approach did indeed allow the visualization of tissues that comprise the artery walls.

Optical Coherence Tomography (OCT), as described in U.S. Pat. No. 5,321,501, which is hereby incorporated by reference, is similar to ultrasonic imaging but uses reflected infrared light to create images instead of echoes from sound waves. As with ultrasound technology, it can be incorporated into an ~1 mm diameter catheter and make images of the vessel wall in addition to the vessel lumen.

Although some mechanically steered IVUS and catheter-based OCT imaging systems create images that are a few degrees off of the perpendicular to the axis of the catheter, these systems are constructed in this way so as to minimize the reflections from the catheter sheath. The size of the reflection is greatest when it encounters the catheter sheath exactly perpendicular to the direction of propagation. Typically, these catheters image ~+5 to −5 degrees from the perpendicular to the catheter axis. Since these images are nearly planar, they are displayed as two-dimensional images on a video monitor. However, in order to see the tissue distal to the tip of the catheter a greater angle from perpendicular must be employed. This results in a conical forward-looking surface that is swept out in front of the transducer or optical fiber. U.S. patent application Ser. No. 11/053,141, which is hereby incorporated by reference, teaches a number of methods for displaying such images using hue, saturation, and intensity of image data to give the impression of a non-planar image.

An excellent review of prior art imaging systems can be found in Bom et. al. "Early and Recent Intraluminal Ultrasound Devices", International Journal of Cardiac Imaging, Vol. 4 1989, pp. 79-88 (hereinafter "Bom article"), which is hereby incorporated by reference. The Bom article discusses different approaches to making intraluminal images that have been tried over the years. With respect to IVUS imaging specifically, many patents exist. For example, U.S. Pat. No. 4,794,931 to Yock, which is hereby incorporated by reference, teaches both an intravascular ultrasonic imaging device, and a combined imaging and therapeutic device, and its use for guiding therapy. The catheters taught create images that are planar in nature and are intended to help guide the removal of atherosclerotic tissue by means of a circular cutting element. Continuations of this patent cover other forms of therapy guidance.

Commercially available IVUS products today create two-dimensional images that are approximately perpendicular to a longitudinal axis of the catheter. With the addition of a motorized mechanical pullback sled as discussed in U.S. Pat. No. 5,361,768, which is hereby incorporated by reference, the catheter can collect these planar images as the catheter is translated (withdrawn) from the vessel. The catheter pullback may also be done by hand. This, in effect, results in a spiral sampling of three-dimensional space that can then be displayed in various ways. Once the data has been collected, the three-dimensional volume can be re-sectioned along the longitudinal axis into what is often referred to as a Longitudinal Mode (L-Mode) image, which is just a longitudinal slice through the vessel. The primary purpose, however, of these three-dimensional IVUS images is to measure the total tissue volume of the atherosclerotic plaque. The segmentation of the imaging data into various tissue and plaque components may now be done automatically by a computer algorithm, thereby saving the operator from the tedious task of tracing the borders of the various tissue components, as discussed in, "Pre-intervention Lesion Remodeling Affects Operative Mechanisms of Balloon Optimized Directional Coronary Atherectomy Procedures: A Volumetric Study With Three Dimensional Intravascular Ultrasound," Heart 2000; 83, 192-197, which is hereby incorporated by reference.

In some applications, however, it is advantageous to view the tissue in front of, or distal to, the catheter tip. Two-dimensional forward-looking IVUS imaging has been documented by a number of authors. In Evans et al., "Arterial Imaging with a New Forward-Viewing Intravascular Ultrasound Catheter, I, Initial Studies," Circulation, vol. 89, No. 2, pp. 712-717, February 1994, which is hereby incorporated by reference, a mechanically wobbled transducer sweeps out a forward-looking, tomographic, two-dimensional image which is displayed using scan conversion techniques common in the ultrasound industry.

A companion paper authored by Ng and titled, "Arterial Imaging With a New Forward-Viewing Intravascular Ultrasound Catheter, II Three-Dimensional Reconstruction and Display of Data," which is hereby incorporated by reference, addresses the display of the image information. By using a forward-looking transducer and rotating it on the catheter axis, a full three-dimensional conical data set is obtained. From the data set, C-Scan (two-dimensional cross-sections parallel to the transducer face) or vessel cross-sectional images are then reconstructed. After manually tracing the vessel wall borders, and spatially orienting the component two-dimensional images, they rendered a three-dimensional surface perspective of the vessel.

Another paper titled, "Three-Dimensional Forward-Viewing Intravascular Ultrasound Imaging of Human in Vitro" by Gatzoulis et al., which is hereby incorporated by reference, describes a similar mechanically wobbled transducer at the end of a catheter using post processing software to display sections in both the complete three-dimensional rendered volumes, B-Scan (two-dimensional cross-sections perpendicular to the face of the transducer) format sections, and C-scan format sections.

Further, U.S. Pat. No. 5,651,366 to Liang et al., which is hereby incorporated by reference, patented a device for making forward-looking images distal to the tip of an intravascular catheter. Not only is the diagnosis of disease envisioned, but the guidance of therapy as well. The Liang catheter employs a mirror in a distal tip of the catheter that reflects an ultrasound beam from a transducer that is in relative motion to the mirror. With the specified geometry, an approximately sector format is created to image the tissue in front of the catheter.

In a 1991 paper titled, "Investigation of a Forward-Looking IVUS Imaging Transducer" by Lee and Benekeser, which is hereby incorporated by reference, the concept of a forward-looking intravascular imaging transducer is described. In this case, the transmitted sound is reflected off a conical mirror to create a conical scan pattern in front of the catheter. No discussion of how one should accurately display the three-dimensional images is included in the manuscript. Presumably, the conical section would be displayed as a conventional IVUS two-dimensional image.

U.S. Pat. No. 6,066,096 to Smith et al., which is hereby incorporated by reference, teaches an electronically steered two-dimensional phased array transducer on the end of a catheter that can incorporate both diagnostic and therapeutic devices. This transducer, in one embodiment, is a forward-looking imaging system. This patent cites prior art that employs C-Scan displays and B-Scan displays to present any plane in the field of view.

U.S. Pat. Nos. 6,457,365 and 6,780,157, which are hereby incorporated by reference, teach a combination side-looking and forward-looking catheter based imaging system. These patents propose two techniques for displaying the forward-looking three-dimensional image data: B-Scans and C-Scans.

Optical Coherence Tomography (OCT) is analogous to ultrasonic imaging but uses light waves instead of sound waves to make images. Since the speed of light is much faster than the speed of sound, simple electronic gating techniques are not adequate for separating the reflections that emanate from the tissues at varying depths. Instead, an interferometer is used, but the rest of the signal processing is much the same as in ultrasonic imaging. Both OCT and IVUS can provide images from the distal tip of a catheter and both are able to guide interventional therapeutic procedures. The display options for intravascular ultrasonic imaging can all be readily applied to intravascular OCT imaging by one of ordinary skill in the art.

Three-dimensional rendering of both medical and non-medical images is common. Three-dimensional image rendering is a process of converting the collected image data in a manner that is amenable to human understanding, while preserving the integrity, intensity, and geometric accuracy of the image information.

In medical imaging, displays tend to fall into two general categories. The first is a surface rendering technique, where an organ surface, or a tissue surface, is detected from the image data and the surface of the tissue is displayed rather than the tissue itself. In these surface renderings, in addition to creating a three-dimensional perspective, one frequently adds lighting, shading, and/or texture to enhance the perception that one is observing a three-dimensional object.

A second technique involves simply selecting any two-dimensional slice from the three-dimensional volume and displaying that image plane on a monitor. In the case of ultrasonic imaging, these two-dimensional planes are referred to as B-Scans if they are in the plane that the sound waves traveled or C-Scans if they are perpendicular to the plane that the sound waves originally traveled. For other medical imaging modalities, they are simply referred to as cut planes or re-sampled planes.

An alternative three-dimensional display technique that allows the observer to view a three-dimensional object from the perspective of inside the object is taught in U.S. Pat. No. 5,606,454 to Williams et al., which is hereby incorporated by reference. This approach may have particular appeal for intraluminal imaging, where the structure to be displayed is in fact hollow.

The above references are incorporated by reference herein where appropriate for appropriate teachings of additional or alternative details, features and/or technical background.

SUMMARY OF THE INVENTION

An object of the invention is to solve at least the above problems and/or disadvantages and to provide at least the advantages described hereinafter.

The invention is directed to an apparatus and method for rendering for display forward-looking image data.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The patent or application file contains at least one drawing executed in color. Copies of this patent or patent application publication with color drawing(s) will be provided by the Patent Office upon request and payment of the necessary fee.

The invention will be described in detail with reference to the following drawings in which like reference numerals refer to like elements wherein.

DETAILED DESCRIPTION OF PREFERRED EMBODIMENTS

Figure 1:
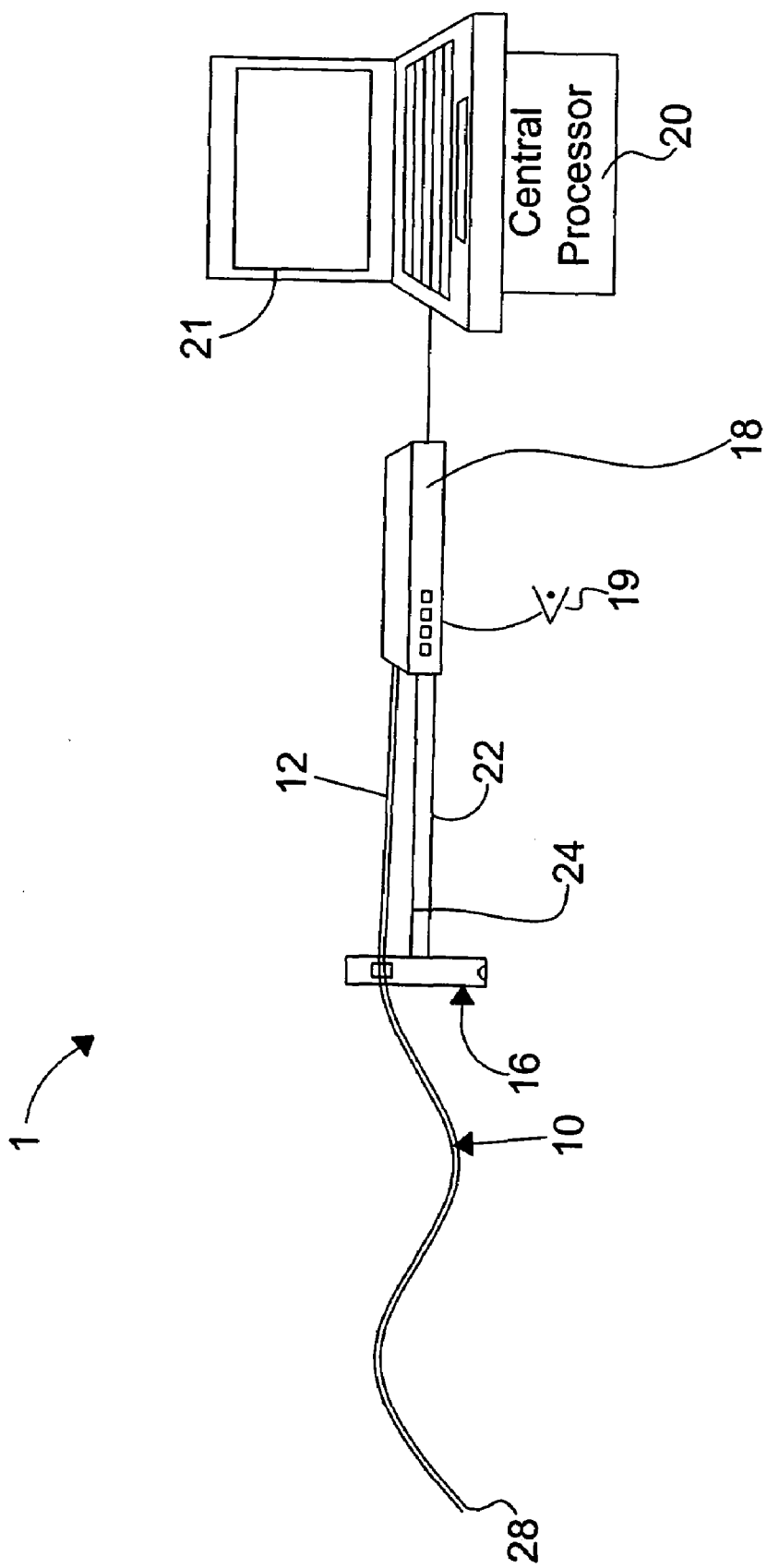
FIG. 1 is a schematic diagram of a IVUS imaging system according to an embodiment of the invention.

The invention is directed to rendering for display a conical forward-looking image on a two-dimensional video monitor in a manner that conveys to an operator the three-dimensional nature of the information. The invention provides a novel imaging modality that allows visualization of a forward-looking section of, for example, a vessel for the purpose of guiding a catheter or other based interventions. The invention may not only reduce the number of emergency by-pass surgeries necessary to repair artery perforations but, more importantly, may facilitate minimally invasive treatment of a higher percentage of coronary artery lesions, thereby avoiding a far more expensive coronary bypass operation.

Further, certain embodiments of the invention are directed to an apparatus and a method that geometrically accurately display conical forward-looking image data so that an observer can immediately assimilate the information being presented and make more efficient and effective diagnostic and therapeutic decisions. The display is neither a B-Scan format nor a C-Scan format nor even a three-dimensional surface rendering. The image data is displayed as though it was on a surface of a three-dimensional geometric model, in one embodiment a cone. As the image is re-scanned, new image data may replace the previous image data in the correct geometric location on the surface of the three-dimensional geometric model, in one embodiment the conical surface.

A nutating motion may be employed to enhance visualization of the image data by an observer. In one embodiment where the three-dimensional geometric model is a cone, the nutating motion would give an observer the impression that the display is, in fact, a conical surface. Lighting and/or shading may also be used to further enhance the impression of a three-dimensional object. The nutation may be at a fixed rotation rate or it may be matched to a rotation of the image device so that when image data is updated the nutation angle is, for example, ~180 degrees out of phase with the newest image data. Alternatively, the new image data may be exactly in phase with the nutation angle.

In one embodiment in which the three-dimensional geometric model is a cone, an angle between an axis of the cone and a line perpendicular to the image display is made sufficiently small with respect to the cone angle to prevent the nutation of the entire cone from blocking the observer's view of the back side of the cone. This has the advantage of avoiding the computational burden of incorporating a hidden line removal algorithm.

In the case where the apparatus and/or method according to embodiments of the invention is used to assist in positioning a diagnostic and/or therapeutic tool or device, a representative marking may be superimposed on the surface of the three-dimensional geometric model to inform the observer where the tool or device will be active.

Further, certain embodiments of the invention are directed to a method and apparatus for rendering for display image data from forward-looking intracavity transducers that acquire the image data in a three-dimensional conical scan format. The data may be displayed in real time and may be nutated about an axis of the device's rotation to provide visual cues to the three-dimensional conical nature of the image. A nutation angle can be controlled either automatically based on an angle of the newest incoming data, automatically based on a periodic time-varying sweep of the nutation angle, or manually based on user input, for example, from a pointing device.

A three-dimensional geometric model of the conical scan format may be constructed, then transformed into two-dimensional space via rotation, translation, scaling, and projection. A nutation angle may be used to create a composite rotation sequence, which may be applied to the three-dimensional conical model and results in the longitudinal axis of the cone being tilted in the desired direction. The image data may be scan-converted (i.e. rasterized) in accordance with the transformed model. The resulting scan-converted image is a two-dimensional representation of a three-dimensional conical scan format.

Although a primary visual cue that the image is three-dimensional is the nutation angle which is varied, additional cues may be added. For example, lighting, shading, and/or texture may be added to provide additional information pertaining to the orientation of the surfaces of the cone. For example, surfaces whose normals point roughly in the direction of the viewer will "reflect" more light and appear brighter than surfaces whose normals point away from the viewer.

Additionally, certain embodiments of the invention include a method and apparatus for rendering for display image data from a forward-looking intracavity transducer using rendering techniques that provide visual cues to a three-dimensional conical scan format of the acquired image data. Forward-looking transducers are useful in visualizing what lies ahead of, for example, a catheter, endoscope, or laparoscope, which is especially important when a therapeutic modality is located at a distal-most end of such a device. The visual cues may include, but are not limited to, nutating an axis of transducer rotation, either automatically or manually, such that the conical scan format of the image is apparent. Using this method and apparatus to render such an image data set avoids the geometric distortion that occurs when data from a forward-looking transducer is rendered with a traditional planar scan-conversion algorithm.

The invention relates generally to the field of medical devices and more specifically to the field of interventional medicine. The invention provides for an accurate depiction of three-dimensional spatial orientation of all points in an image, thereby allowing for more accurate diagnosis and treatment of disease. One specific application that will be used for the purpose of explaining the invention is Interventional Cardiology; however, the invention may be utilized for any application for which rendering for display collected image data to assist a user in visualizing the image data would be useful or advantageous.

The imaging modality frequently chosen for Interventional Cardiology is IVUS; however, the image may be utilized with other image data collection modalities or techniques. While IVUS is a well known diagnostic imaging technique, it can also serve as a therapeutic guidance tool. For example, expansion of an angioplasty balloon or deployment of a stent can be visualized in real-time to improve clinical outcome. Other therapeutic techniques and devices would also benefit from an operator's ability to visualize therapy as it progresses. In some cases, therapeutic action takes place at the very distal tip of a catheter. Such a situation can occur when using, for example, laser ablation, radio-frequency ablation, biopsy forceps, and biopsy needles. To optimally guide these therapies and diagnostic procedures it is beneficial to have an accurate depiction of the tissue involved which can lie distal to the catheter tip.

FIG. 1 is a schematic diagram of an IVUS imaging system according to an embodiment of the invention. The system 1 includes a catheter 10. The distal end or tip 28 is adapted to be inserted into a patient and is constructed to be navigable through the patient's vasculature to advance the distal end 28 to an area or site of interest. The distal tip 28 of the catheter 10 carrier an ultrasound transducer (not shown). Further, the distal end 28 may also carry an ablation electrode (not shown) adapted to ablate an obstructed portion of a vessel or other body cavity. The proximal end of the catheter 10 is designed to remain outside of the patient where it can be associated with an angle encoder 16 and can be manipulated by an operator, such as an interventionalist or physician.

The system 1 further includes an electronics module 18 that includes circuitry and software for generating signals for operating the system 1 and for receiving and processing signals from resulting ultrasound echoes, as well as for generating an RF ablation signal if an ablation electrode is included in the system. A central processing unit 20 constructs images from the received ultrasound signals and displays the images on a monitor 21. The images may be generated on demand and may be refreshed in response to operator rotation of the catheter 10. The images may be caused to fade after a predetermined time as a reminder to an operator to refresh the image by rotating the catheter 10. The central processing unit 20 may comprise, for example, a laptop or desktop computer or a dedicated embedded processor. Cables 22, 24 may be connected between the angle encoder 16 and the electronics module 18. In one embodiment, the cable 22 carries incremental angle information that is sensed by the angle encoder 16 and cable 24 provides power and ground. Separate cables may run from the catheter 10 to the electronics module 18 and carry ultrasound signals and also RF energy if an ablation electrode is included in the system. In an alternate arrangement (not shown), transducer and RF cables from the catheter 10 may plug into a connector integrated into the angle encoder 16 and then, after pre-amplifying the ultrasound signals, pass the signals through a second connector on the angle encoder 16 to the electronics module 18. This alternate arrangement allows for a shorter catheter cable and, potentially, reduces environmental noise pick-up.

The catheter 10 may be rotated and manipulated entirely under manual control of the operator. Similarly, in the case where an ablation electrode is included in the system 1, initiation of the ablation pulse may be determined by the operator independently of any direct connection with the catheter or the system for sensing catheter rotation. It should be understood that reference to "manual" with respect to control over the application of ablation energy includes any arrangement by which the operator, based on judgment as to the proper location of the ablation electrode, initiates the ablation sequence. Thus, "manual" operation may include a variety of arrangements, including, mechanically controlled switches, for example, a foot switch, or a voice operated control or other means by which the operator can trigger an ablation cycle, for example, by manipulation of pedal 19.

Figure 2A:
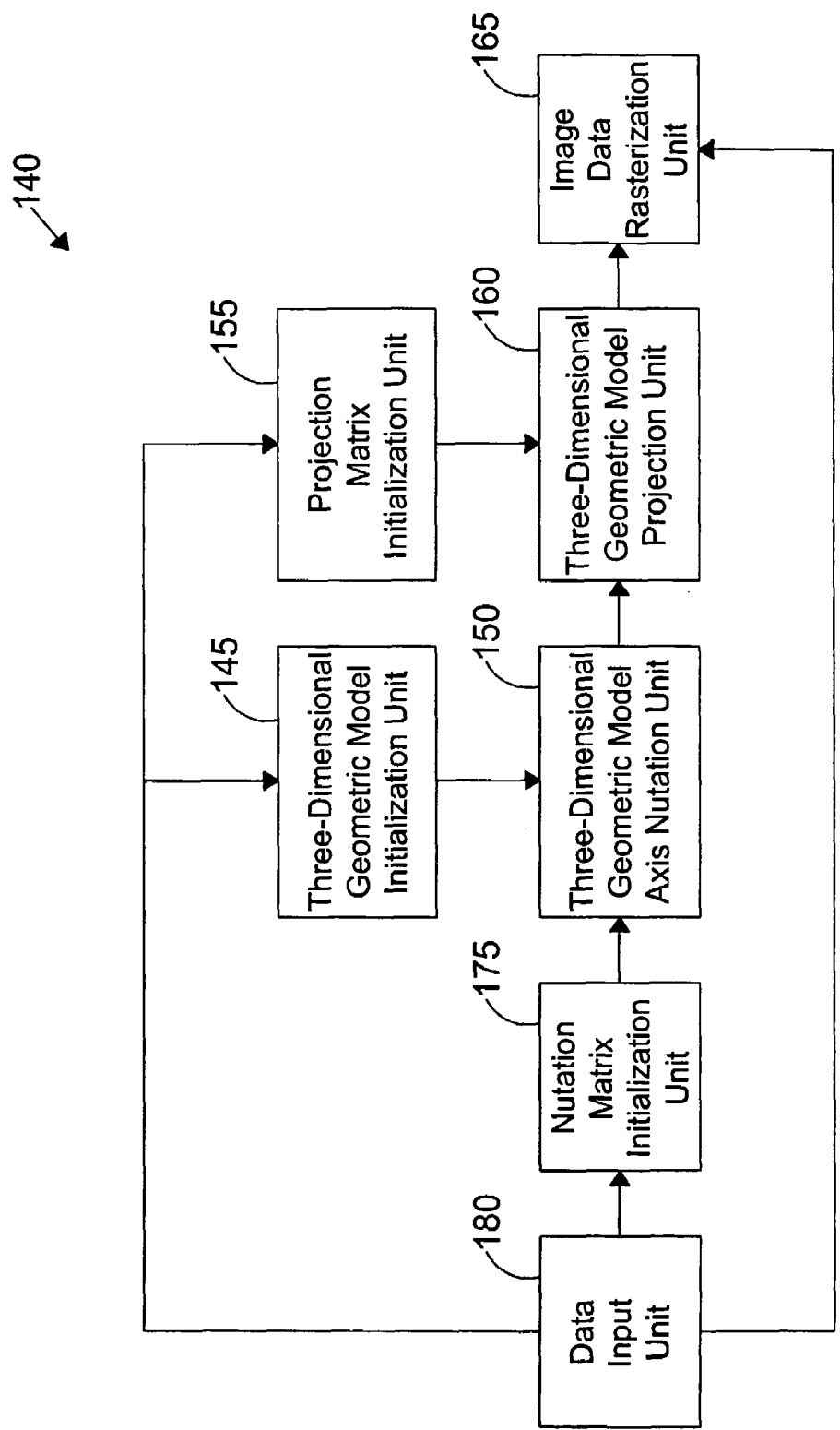
FIG. 2A is a block diagram of a rendering apparatus according to an embodiment of the invention.
Figure 2B:
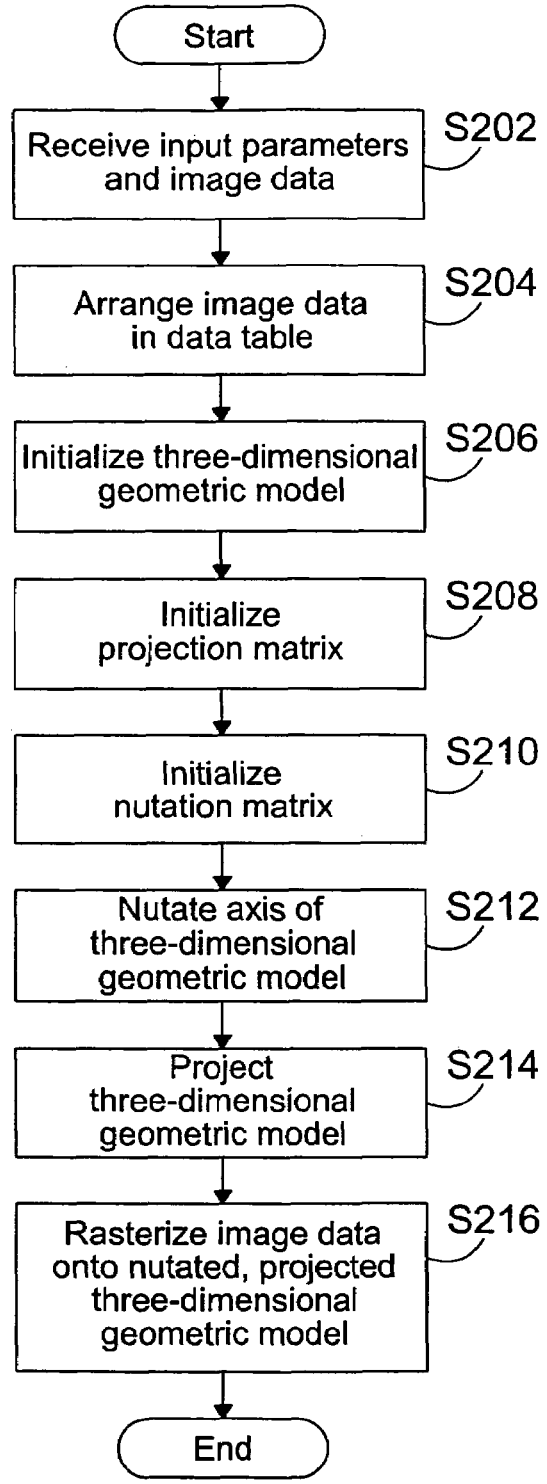
FIG. 2B is a flow chart of a rendering method according to an embodiment of the invention.

FIGS. 2A and 2B disclose a block diagram of a rendering apparatus and a flow chart of a rendering method, respectively, according to embodiments of the invention. As shown in FIG. 2A, the rendering apparatus 140 includes a data input unit 180 in which image data is received or input from an imaging system, such as the IVUS system shown in FIG. 1. The data input unit 180 may organize the image data into a data table, such as that shown in FIG. 6. The data input unit 180 may also receive parameters set by a user or set and/or calculated by the imaging system. Such parameters may include the forward scanning angle, the radius of the base, the observer distance, the magnitude of nutation, the samples per line, the lines per frame.

The rendering apparatus 140 further includes a three-dimensional geometric model initialization unit 145, a projection matrix initialization unit 155, and a nutation matrix initialization unit 175. The three-dimensional geometric model initialization unit 145 outputs a three-dimensional geometric model, in one embodiment, a conical polyhedron, while the projection matrix initialization unit 155 and the nutation matrix initialization unit 175 output a projection matrix and a nutation matrix, respectively. The present application discloses using a conical polyhedron as the three-dimensional geometric model, for example, however, other three-dimensional geometric models may be appropriate based on the particular application. The rendering apparatus 140 further includes a three-dimensional geometric model axis nutation unit 150, which receives the three-dimensional geometric model, in one embodiment a conical polyhedron, and the nutation matrix from the three-dimensional geometric model initialization unit 145 and the nutation matrix initialization unit 175, respectively, and outputs a nutated, three-dimensional geometric model, in one embodiment a nutated conical polyhedron. The nutated, three-dimensional geometric model is forwarded to a three-dimensional geometric model projection unit 160, which also receives the projection matrix from the projection matrix initialization unit 155. The three-dimensional geometric model projection unit 160 outputs a nutated, projected three-dimensional geometric model, in one embodiment a nutated, projected, conical polyhedron, to an image data rasterization unit 165.

Figures 5, 6:
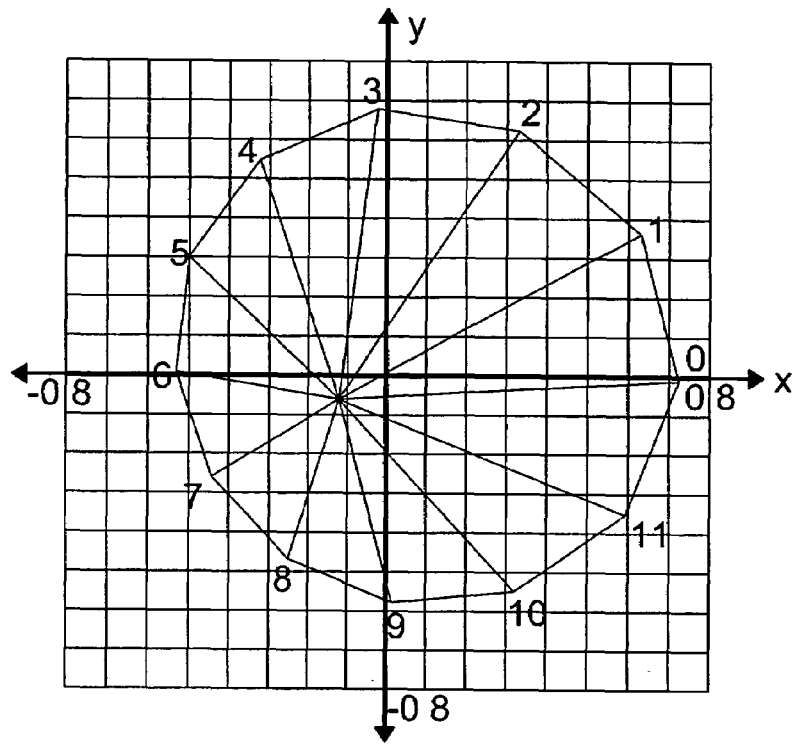
FIG. 5 illustrates a perspective projection of an exemplary nutated version of the conical polyhedron of FIG. 4A.
FIG. 6 illustrates an exemplary data table according to the invention.
Figure 7A:
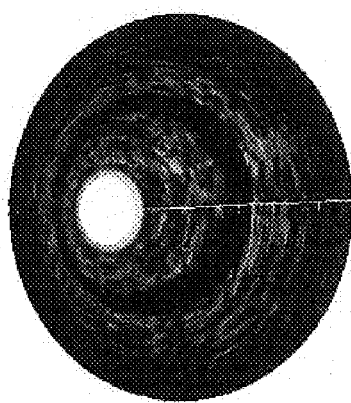
FIGS. 7A-7F are still frames taken from an exemplary display utilizing an apparatus and method according to the embodiments of the invention.
Figure 7B:
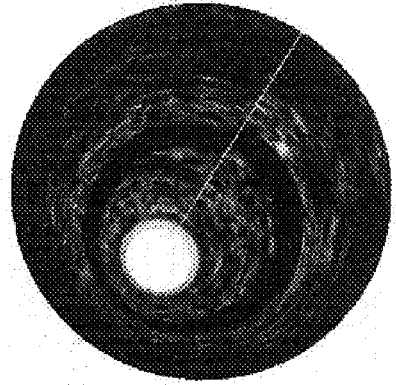
Figure 7C:
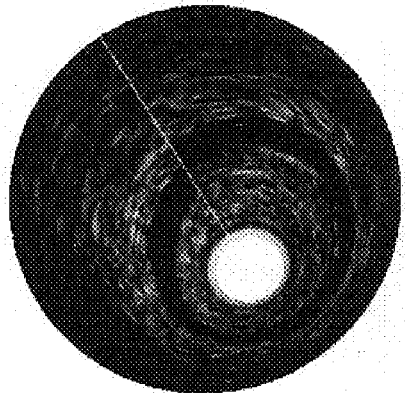
Figure 7D:
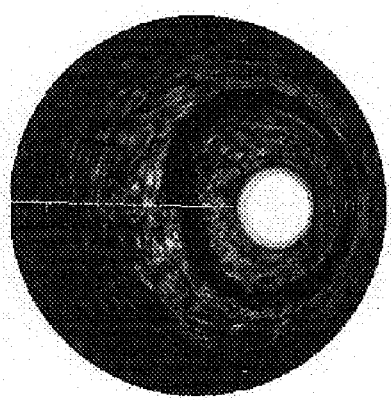
Figure 7E:
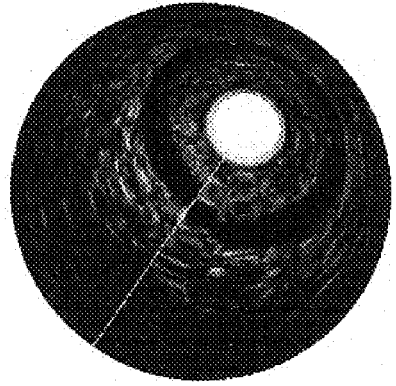
Figure 7F:
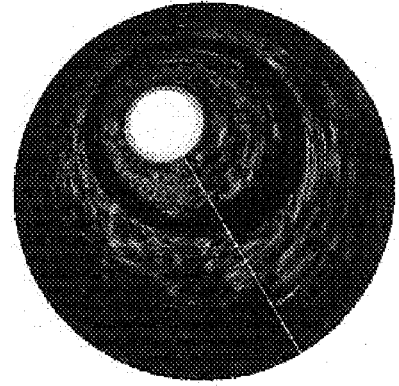

As set forth above, image data collected by the system 1 is received by the data input unit 180 and arranged in a data table, such as that shown in FIG. 6, including angle and image data for each scan line. The image data is forwarded to the image data rasterization unit 165 by the data input unit 180. The image data is then rasterized by the image data rasterization unit 165 onto the nutated, projected three-dimensional geometric model, in one embodiment a nutated, projected, conical polyhedron output by the three-dimensional geometric model projection unit 160. The data input unit 180 also provides the leading scan line angle to the nutation matrix initialization unit 175 to be used in calculating the nutation matrix.

As set forth above, FIG. 2B is a block diagram of a rendering method according to an embodiment of the invention. First, parameters, such as the forward scanning angle, the radius of the base, the observer distance, the magnitude of nutation, the samples per line, the lines per frame, and the image data are received input by a user or an imaging system, such as that shown in FIG. 1, in step S202. In step S204, the image data is arranged in a data table, such as that shown in FIG. 6, including angle and image data for each scan line.

Then, using the received parameters, a three-dimensional geometric model, projection matrix, and nutation matrix are initialized in steps S204, S208, and S210, respectively. The order of the steps S204-S210 is not important and thus the order of these steps may be changed. Next, using the three-dimensional geometric model, a conical polyhedron in one embodiment, created in step S206 and the nutation matrix initialized in step S210, an axis of the three-dimensional geometric model, in one embodiment a conical polyhedron, is nutated to create a nutated, three-dimensional geometric model, in one embodiment a nutated, conical polyhedron, in step S212. In step S214, the three-dimensional geometric model is projected using the three-dimensional geometric model projection matrix initialized in step S208. In step S216, the image data is rasterized onto the nutated, projected, three-dimensional geometric model. The various processing steps of FIG. 2B will be discussed in further detail below.

The rendering apparatus 140 of FIG. 2A and rendering method of FIG. 2B are essentially a pipeline for processing three-dimensional coordinates as well as image data. Referring to FIG. 2A, the three-dimensional coordinates originate in the three-dimensional geometric model initialization unit 145, and are subsequently transformed into two-dimensional coordinates by the three-dimensional geometric model axis nutation unit 150 and the three-dimensional geometric model projection unit 160. The transformed coordinates are then sent to the image data rasterization unit 165 which rasterizes the image data onto the nutated, projected, three-dimensional geometric model for scan conversion.

The overall pipeline depicted in FIGS. 2A and 2B is a variation of a three-dimensional rendering pipeline as practiced in the field of computer graphics. The use of homogeneous coordinates is well-established in this field, and the invention uses such coordinates. In the invention, three-dimensional coordinates are "homogenized" in step S212 by adding a fourth coordinate w, which is initialized to one. Thus, three-dimensional coordinates (x, y, z) are promoted to homogeneous coordinates (x, y, z, 1). These homogeneous coordinates are demoted back to three-dimensional coordinates at the conclusion of step S214 such that coordinates of the form (x, y, z, w) are renormalized to (x/w, y/w, z/w). This demotion or renormalization can also be thought of as the projection of homogeneous coordinates of the form (x, y, z, w) into the w=K plane, where K is a constant, often one.

Transformations of objects from so-called "object space" to "image space" are accomplished by multiplying object-space coordinates by one or more transformation matrices representing object rotation, scaling, translation, observer location and orientation, and three-dimensional to two-dimensional projection. The transformation matrices may be premultiplied into a single matrix for efficiency. Because matrix multiplication is not commutative, there are two different conventions for transforming coordinates. The traditional convention as taught in mathematics and computer graphics textbooks is to postmultiply the transformation matrices by column coordinate vectors. The other convention is to premultiply the transformation matrices by row coordinate vectors. The transformation matrices must be transposed to go from one convention to the other, as is known to practitioners skilled in the field of computer graphics. Embodiments of the invention use the traditional convention of postmultiplying transformation matrices by column coordinate vectors. This is illustrated by the following equation (1).

$$\begin{bmatrix} x' \\ y' \\ z' \\ w' \end{bmatrix} = \begin{bmatrix} t_{11} & t_{12} & t_{13} & t_{14} \\ t_{21} & t_{22} & t_{23} & t_{24} \\ t_{31} & t_{32} & t_{33} & t_{34} \\ t_{41} & t_{42} & t_{43} & t_{44} \end{bmatrix} \cdot \begin{bmatrix} x \\ y \\ z \\ 1 \end{bmatrix} \quad \text{Equation (1)}$$

where
$t_{11}$ through $t_{44}$ constitute aggregate transformation coefficients
x, y, and z are coordinates of the point in three-dimensional space
x', y', z', and w' are transformed homogeneous coordinates In order to obtain the final two-dimensional coordinates in image space, the transformed coordinates are renormalized to the form (x'/w', y'/w', z'/w'), and then the z'/w' terms are simply dropped, yielding two-dimensional coordinates of the form (x'/w', y'/w'). These may have to be further and trivially mapped to physical device coordinates suitable for addressing video monitor pixels.

The proper representation and manipulation of three-dimensional objects requires the selection and consistent use of either a right-handed or left-handed coordinate system. In a right-handed coordinate system, the (x, y, z) axes are arranged such that a rotation of the x-axis into the y-axis (i.e. clockwise through 90°) corresponds to the rotation of a right-handed screw advancing in the positive z direction. In the context of a video monitor, when an observer is looking at the monitor, the x-axis points to the right, the y-axis points upward, and the z-axis comes "out" of the monitor toward the observer. This means that the z-coordinates of most objects in three-dimensional space are negative, i.e. "inside" the monitor. Because of this somewhat awkward situation, three-dimensional computer graphics systems, such as software libraries, often use left-handed coordinate systems in order to locate objects in positive z-coordinate space. Nonetheless, mathematics and computer graphics textbooks traditionally teach right-handed coordinate systems, and as such, the discussion of the embodiments of the invention will also use a right-handed coordinate system. A practitioner skilled in the field of computer graphics will be able to easily convert between the two coordinate systems.

Figure 4B:
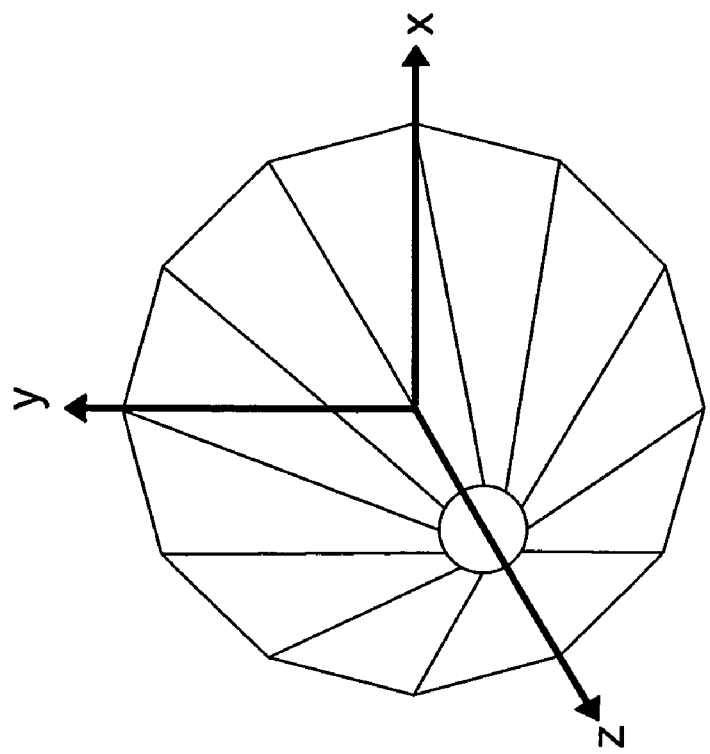
FIG. 4B is an oblique parallel projection of another exemplary non-nutated, conical polyhedron.
Figure 4A:
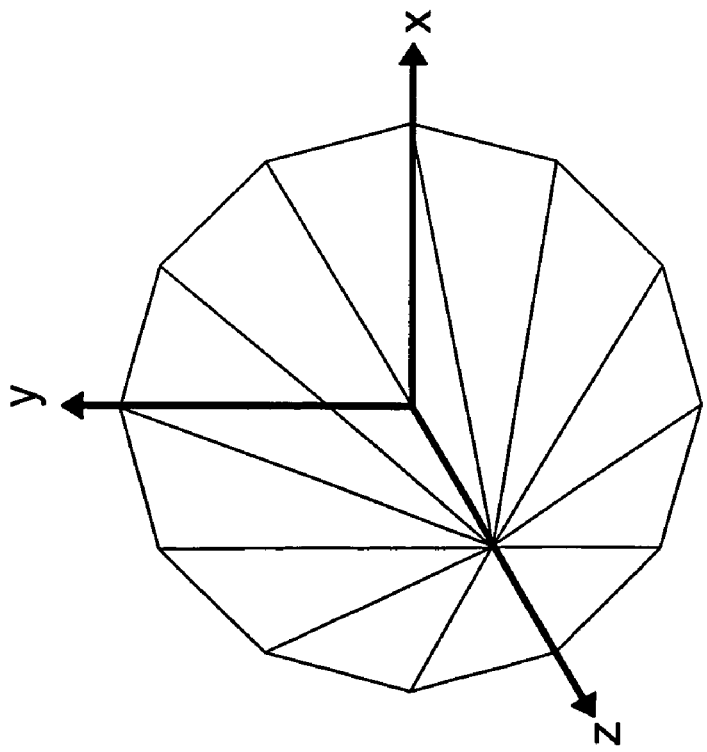
FIG. 4A is an oblique parallel projection of an exemplary non-nutated, conical polyhedron.

In step S206 in FIG. 2B, a three-dimensional geometric model is created of the scanning surface, in this exemplary embodiment a conical scanning surface. In one embodiment, this cone is approximated by a series of connected planar, isosceles triangular surfaces which define a polyhedron, as shown in FIG. 4A. In one particular alternative embodiment, the apex of the cone is open because the scan lines do not begin on the longitudinal axis of the imaging catheter; rather, the scan lines begin at a radial offset from this axis. FIG. 4B shows an exemplary open conical polyhedron. In this alternative embodiment, the open cone is approximated by a series of connected planar, regular trapezoidal surfaces which define a polyhedron. In additional alternative embodiments, the cone may be approximated by various types of parametric bicubic surface patches, including but not limited to Hemite surfaces, Bézier surfaces, and B-Spline surfaces. The cone may also be modeled exactly by using either implicit or explicit surface equations, including the implicitly defined family of quadric surfaces. A survey of several surface representations is presented by Foley et al. in "Computer Graphic Principles and Practice," Second Edition, Addison-Wesley Publishing Company, 1990, which is hereby incorporated by reference.

It is convenient, but not necessary, to choose the number of triangles to be equal to the number of scan lines comprising a complete ~360° rotation of the catheter. If this is the case, then each scan line represents a shared edge of two adjacent triangles in the polyhedron. Furthermore, two adjacent scan lines represent two equal sides of a single isosceles triangle. All scan lines emanate from the apex of the polyhedron and diverge as they approach the base.

Figure 3:
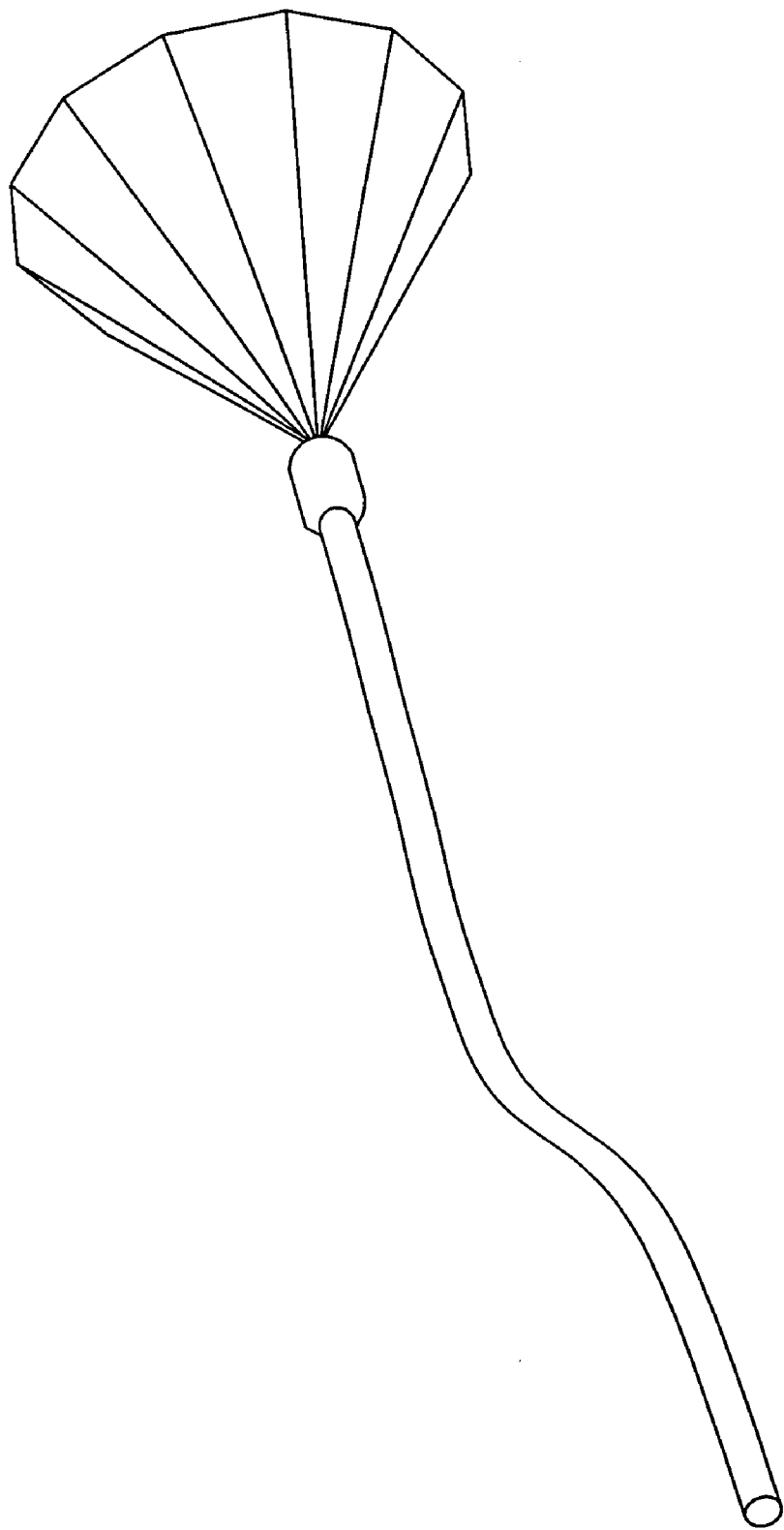
FIG. 3 is a perspective view of a catheter and transducer assembly along with a depiction of a forward-scanning cone.

As the number of triangles increases, the polyhedron approaches a true cone, but at the cost of more computational and storage resources required to realize the apparatus. Conversely, defining the polyhedron with fewer triangles results in a rougher approximation of a cone, but the computational and storage resources required are reduced. As an illustrative example only, FIG. 3 shows a catheter and transducer assembly along with a depiction of a forward-scanning polyhedron. FIG. 4A, discussed above, shows just the polyhedron with 12 isosceles triangles corresponding to 12 scan lines per revolution. Similarly, FIG. 4B, discussed above, shows just the polyhedron with 12 regular trapezoids corresponding to 12 scan lines per revolution; the hole at the apex of the polyhedron in FIG. 4B is an area adjacent the catheter and transducer assembly. The scan lines and triangles are spaced at ~30° angular increments. This example is illustrative only because approximating a cone with just 12 isosceles triangles is generally too rough an approximation to produce a realistic-looking cone. Further, 12 scan lines per catheter revolution would dramatically undersample the image with respect to the inherent lateral resolution of the transducer, resulting in poor image quality. One embodiment of the method and apparatus according to the invention uses 400 isosceles triangles corresponding to 400 scan lines per catheter revolution. This results in scan lines and triangles spaced at ~0.9° angular increments.

When assigning three-dimensional coordinates to the geometric model, its size, orientation, and location must be specified. First, it is convenient to define a small number of variables to define the size of the geometric model. Let ψ=forward scanning angle
R=radius of cone at base
H=height of cone=R*tan(ψ)

In order to orient the geometric model such that the apex points directly toward the observer, when the image is not being nutated, its longitudinal axis may be defined to be coincident with the z-axis, with the apex of the model having a more positive z-coordinate than the z-coordinates of the points on the base.

To locate the geometric model, the origin may be defined to be the center of the base of the geometric model, i.e. the point along its longitudinal axis in the plane of the base. This point has the three-dimensional coordinates (x, y, z)=(0, 0, 0). Note that in order for nutations to be symmetrical about the longitudinal axis of the model, the x- and y-coordinates must be equal to zero. However, the z-coordinate may be redefined to vary the visual effect of nutation. For example, defining the origin at the apex results in the apex remaining at a fixed location and the base gyrating when the image is nutated, while defining the origin at the center of the base results in the apex gyrating and the base gyrating relatively less. When projecting the model into two dimensions for display, the choice of the z-coordinate for the origin has an effect on the total amount of screen area required to display the image under all possible nutation angles. The value of this coordinate that minimizes the screen area depends on the parameters of the geometric model, but the screen area is never minimized when the origin is defined at the apex.

With the center of the base of the geometric model at (0, 0, 0), the location of the apex is (0, 0, +H). Note that the observer must be located further "back" than +H to avoid being "inside" the geometric model. This is accomplished by a simple translation of −H, plus any additional desired observer distance. The remaining coordinates are located along the circular perimeter of the base of the polyhedron. Let L=number of scan lines per complete catheter rotation
A=angle subtended per scan line=360°/L
n=variable used to represent the scan line number, ranges from 0 to L−1
θ=scan line angle=n*A Then, the position of the endpoint for scan line n may be provided by equation (2) as follows:

$$P_n(x,y,z) = (R\cos(\theta), R\sin(\theta), 0) \quad \text{Equation (2)}$$

An example is provided below:
R=1.0
ψ=30°
H=1.0*tan(30°)=0.577
Apex of cone $P_A(x, y, z)$=(0, 0, 0.577)
L=12
A=360°/12=30°

The endpoints for each scan line are specified in the following table (1) below.

TABLE (1)

| n | θ = n * A | x = cos(θ) | y = sin(θ) | z = 0 |
|---|---|---|---|---|
| Apex | N/A | 0.000 | 0.000 | 0.577 |
| 0 | 0.0 | 1.000 | 0.000 | 0.000 |
| 1 | 30.0 | 0.866 | 0.500 | 0.000 |
| 2 | 60.0 | 0.500 | 0.866 | 0.000 |
| 3 | 90.0 | 0.000 | 1.000 | 0.000 |
| 4 | 120.0 | −0.500 | 0.866 | 0.000 |
| 5 | 150.0 | −0.866 | 0.500 | 0.000 |
| 6 | 180.0 | −1.000 | 0.000 | 0.000 |
| 7 | 210.0 | −0.866 | −0.500 | 0.000 |
| 8 | 240.0 | −0.500 | −0.866 | 0.000 |
| 9 | 270.0 | 0.000 | −1.000 | 0.000 |
| 10 | 300.0 | 0.500 | −0.866 | 0.000 |
| 11 | 330.0 | 0.866 | −0.500 | 0.000 |

The three-dimensional polyhedron must be projected from three-dimensional object space into two-dimensional image space. In one embodiment of the method and apparatus according to the invention, a perspective projection is used to provide depth cues to the observer. The simplest form for a perspective projection matrix where the center of projection is at the origin (0, 0, 0) and the projection plane is normal to the z-axis and at a distance z=d may be provided by equation (3) as follows:

$$P = \begin{bmatrix} 1 & 0 & 0 & 0 \\ 0 & 1 & 0 & 0 \\ 0 & 0 & 1 & 0 \\ 0 & 0 & 1/d & 0 \end{bmatrix} \quad \text{Equation (3)}$$

With d=−1, the projection matrix then simplifies as shown in exemplary equation (4) as follows:

$$P = \begin{bmatrix} 1 & 0 & 0 & 0 \\ 0 & 1 & 0 & 0 \\ 0 & 0 & 1 & 0 \\ 0 & 0 & -1 & 0 \end{bmatrix} \quad \text{Equation (4)}$$

An alternative form for a perspective projection matrix places the projection plane normal to the z-axis at z=0 and the center of projection at (0, 0, −d) and may be provided by equation (5) as follows:

$$P' = \begin{bmatrix} 1 & 0 & 0 & 0 \\ 0 & 1 & 0 & 0 \\ 0 & 0 & 0 & 0 \\ 0 & 0 & 1/d & 1 \end{bmatrix} \quad \text{Equation (5)}$$

This form allows the distance d from the center of projection to the projection plane to tend to infinity. As the distance d approaches infinity, the perspective projection becomes a parallel projection. In an alternative embodiment of the method and apparatus according to the invention, a perspective projection matrix in the form of equation (5) is used. In an additional alternative embodiment, a parallel projection is used by setting d=∞ in equation (5).

In one embodiment of the method and apparatus according to the invention, an observer transformation is also applied which is a translation of the polyhedron in the negative z direction by an observer distance D. The purpose of this translation is to place the polyhedron entirely behind the projection plane, so the polyhedron height H must be added to D. This transformation may be provided by equation (6) as follows:

$$O = \begin{bmatrix} 1 & 0 & 0 & 0 \\ 0 & 1 & 0 & 0 \\ 0 & 0 & 1 & -(D+H) \\ 0 & 0 & 0 & 1 \end{bmatrix} \quad \text{Equation (6)}$$

The composite projection matrix, which includes both the observer transformation and the projection matrices, may be provided by equation (7) as follows:

$$O \cdot P = \begin{bmatrix} 1 & 0 & 0 & 0 \\ 0 & 1 & 0 & 0 \\ 0 & 0 & 1 & -(D+H) \\ 0 & 0 & 0 & 1 \end{bmatrix} \cdot \begin{bmatrix} 1 & 0 & 0 & 0 \\ 0 & 1 & 0 & 0 \\ 0 & 0 & 1 & 0 \\ 0 & 0 & -1 & 0 \end{bmatrix} = \quad \text{Equation (7)}$$

$$\begin{bmatrix} 1 & 0 & 0 & 0 \\ 0 & 1 & 0 & 0 \\ 0 & 0 & 1 & -(D+H) \\ 0 & 0 & -1 & D+H \end{bmatrix}$$

Since matrix multiplication is not commutative, the observer transformation must be applied before the projection. Further, it is equally valid to postmultiply the nutation matrix by the observer transformation matrix as it is to premultiply the projection matrix by the observer transformation matrix. In both cases, the observer transformation must occur after the nutation transformation and before the projection.

In FIG. 2A, the projection matrix is established by the projection matrix initialization unit 155 using the parameters, forward scanning angle, radius at base, and observer distance. The projection matrix is subsequently used by the three-dimensional geometric model projection unit 160 to transform the nutated, three-dimensional geometric model, in this example a polyhedron, into a nutated, projected three-dimensional geometric model.

The means of acquiring ultrasound image data are well understood. For example, U.S. patent application Ser. No. 11/261,635 by Goodnow, et al., which is hereby incorporated by reference, describes the acquisition process for an exemplary IVUS imaging system similar to an exemplary IVUS system which may be utilized with embodiments of the invention. In particular, U.S. patent application Ser. No. 11/261,635 describes the generation of a data table for storing catheter angle and ultrasound image data FIG. 6 depicts an exemplary data table which may be utilized for embodiments of the invention. The data table of FIG. 6 has three columns. The first is simply an index, which may be omitted if the indices are contiguous. The second column is the catheter angle, which is derived from data received from the angle encoder 16 in FIG. 1. The third column is the detected or grayscale ultrasound image data. Note that the data in each of the rows in the third column is actually an array of grayscale samples but that for notational simplicity these arrays are treated as ImageData[n, t]. The number of grayscale samples in conjunction with the sampling rate in samples per second and the speed of sound in water can be used to estimate the scanning depth. A typical scanning depth is ~five millimeters for an exemplary IVUS system, such as that depicted in FIG. 1. A complete data table is defined as a data table with one row for every ultrasound scan line acquired in one complete, ~360° rotation of the catheter.

Referring again to FIG. 2A, the data input unit 180 may control the ultrasound image acquisition process or receive grayscale data from another process, such as an acquisition process in the electronics module 18 shown in FIG. 1. U.S. patent application Ser. No. 11/261,635 describes in detail an exemplary acquisition process. The data input unit 180 creates with the acquired image data either a complete data table or a subset of a complete data table which may be merged with previous data. In a manually rotated imaging system, the data table created by the data input unit 180 is likely to be a subset of a complete data table. A complete data table contains the most recent version of the ultrasound scan lines from each of the angles in one complete, ~360° rotation of the catheter.

Referring again to FIG. 2A, in addition to generating a data table, the data input unit 180 also receives and outputs to the nutation matrix initialization unit 175 the leading scan line angle. The leading scan line angle is defined as the catheter angle corresponding to the most recently acquired ultrasound scan line. The leading scan line angle is used in one embodiment by the nutation matrix initialization unit 175 to compute the magnitude and direction of nutation.

In an IVUS system with a manually rotated catheter, the position of the catheter changes relatively slowly as the operator manipulates the device. One embodiment of the method and apparatus according to the invention takes advantage of this slow, manually controlled rotation by setting the orientation of the longitudinal axis of the geometric model or cone to track the angular position of the catheter. Specifically, the longitudinal axis of the geometric model or cone is tilted to the opposite side or away from the angular position or leading scan line angle of the catheter. When projected into two-dimensional space, this makes the most recently acquired data larger and appear closer to the observer and easier to view. The diametrically opposing data is foreshortened and therefore deemphasized. The amount of tilt with respect to the z-axis is a quantity that is independent of the leading scan line angle and may be a constant. This constant is the magnitude of nutation and is expressed in angular units such as degrees. The overall tilt can be expressed as a rotation about a direction in the (x, y) plane, with the direction specified as a function of the leading scan line angle. For example, if the leading scan line angle is 0° or 180°, then the longitudinal axis of the geometric model or cone is rotated about the y-axis, and if the leading scan line angle is 90° or 270°, then the longitudinal axis of the geometric model or cone is rotated about the x-axis. For angles other than these special cases, the axis of rotation may be given by the normalized direction vector in equation (8) as follows:

$$\bar{u}=\sin(\theta)\hat{\imath}-\cos(\theta)\hat{\jmath} \qquad \text{Equation (8)}$$

where
  θ=Leading scan line angle

From the field of computer graphics, the rotation matrix for a rotation φ about an arbitrary direction given by the direction vector $U=(u_x, u_y, u_z)$ is given by Rodrigues' rotation formula, equation (8) as follows:

$$R = \begin{bmatrix} u_x^2(1-\cos\phi)+\cos\phi & u_x u_y(1-\cos\phi)-u_z\sin\phi & u_x u_z(1-\cos\phi)+u_y\sin\phi & 0 \\ u_x u_y(1-\cos\phi)+u_z\sin\phi & u_y^2(1-\cos\phi)+\cos\phi & u_y u_z(1-\cos\phi)-u_x\sin\phi & 0 \\ u_x u_z(1-\cos\phi)-u_y\sin\phi & u_y u_z(1-\cos\phi)+u_x\sin\phi & u_z^2(1-\cos\phi)+\cos\phi & 0 \\ 0 & 0 & 0 & 1 \end{bmatrix} \qquad \text{Equation (9)}$$

Substituting using equations (10.1), (10.2), and (10.3) as follows:

$$u_x = \sin\theta \qquad \text{Equation (10.1)}$$

$$u_y = -\cos\theta \qquad \text{Equation (10.2)}$$

$$u_z = 0 \qquad \text{Equation (10.3)}$$

the matrix becomes equation (11) as follows:

$$R = \begin{bmatrix} \sin^2\theta\cdot(1-\cos\phi)+\cos\phi & -\sin\theta\cdot\cos\theta\cdot(1-\cos\phi) & -\cos\theta\cdot\sin\phi & 0 \\ -\sin\theta\cdot\cos\theta\cdot(1-\cos\phi) & \cos^2\theta\cdot(1-\cos\phi)+\cos\phi & -\sin\theta\cdot\sin\phi & 0 \\ \cos\theta\cdot\sin\theta & \sin\theta\cdot\sin\phi & \cos\phi & 0 \\ 0 & 0 & 0 & 1 \end{bmatrix} \qquad \text{Equation (11)}$$

Referring to FIG. 2A, the nutation matrix initialization unit 175 computes the nutation matrix according to Equation (11) using the leading scan line angle (θ) and the magnitude of nutation (φ)

Referring again to FIG. 2A, the axis of the three-dimensional geometric model, or in one embodiment vertices of the conical polyhedron, are transformed by the three-dimensional geometric model axis nutation unit 150 and the three-dimensional geometric model projection unit 160 into an axis or vertices for a nutated, projected, three-dimensional geometric model. In one embodiment of the method and apparatus according to the invention, an intermediate vertex stream or nutated, three-dimensional geometric model is produced. In an alternative embodiment, the nutation and projection transformation matrices may be concatenated into a single matrix and vertices from the three-dimensional geometric model are transformed directly into vertices for the nutated, projected, three-dimensional geometric model.

The three-dimensional geometric model axis nutation unit 150 and the three-dimensional geometric model projection unit 160 both transform homogeneous coordinate streams according to equation (1). These equations expand to equation (12) as follows:

$$x'=t_{11}x+t_{12}y+t_{13}z+t_{14}w$$

$$y'=t_{21}x+t_{22}y+t_{23}z+t_{24}w$$

$$z'=t_{31}x+t_{32}y+t_{33}z+t_{34}w$$

$$w'=t_{41}x+t_{42}y+t_{43}z+t_{44}w \qquad \text{Equation (12)}$$

where $t_{11}$ through $t_{44}$ are the coefficients in the nutation matrix used by the three-dimensional geometric model axis nutation unit 150 and $t_{11}$ through $t_{44}$ are the coefficients in the projection matrix used by the three-dimensional geometric model projection unit 160. Note that $w$ is set to one by the three-dimensional geometric model axis nutation unit 150, and to $w''$ by the three-dimensional geometric model projection unit 160.

An example is provided below:

Use the conical polyhedron model defined in Table (1). From this example the polygon height H is 0.577. Also, for illustrative purposes, let D=1.0 (observer distance)

Then, from equation (7), the composite projection matrix is as follows:

$$O \cdot P = \begin{bmatrix} 1 & 0 & 0 & 0 \\ 0 & 1 & 0 & 0 \\ 0 & 0 & 1 & -(D+H) \\ 0 & 0 & -1 & D+H \end{bmatrix} = \begin{bmatrix} 1 & 0 & 0 & 0 \\ 0 & 1 & 0 & 0 \\ 0 & 0 & 1 & -1.577 \\ 0 & 0 & -1 & 1.577 \end{bmatrix}$$

To compute the nutation matrix, for illustrative purposes, let
  θ=30° (leading scan line angle)
  φ=15° (magnitude of nutation)

Then, from equation (11), the nutation matrix is as follows:

$$R = \begin{bmatrix} \sin^2 30° \cdot (1-\cos 15°) + \cos 15° & -\sin 30° \cdot \cos 30° \cdot (1-\cos 15°) & -\cos 30° \cdot \sin 15° & 0 \\ -\sin 30° \cdot \cos 30° \cdot (1-\cos 15°) & \cos^2 30° \cdot (1-\cos 15°) + \cos 15° & -\sin 30° \cdot \sin 15° & 0 \\ \cos 30° \cdot \sin 15° & \sin 30° \cdot \sin 15° & \cos 15° & 0 \\ 0 & 0 & 0 & 1 \end{bmatrix}$$

$$= \begin{bmatrix} 0.974 & -0.015 & -0.224 & 0 \\ -0.015 & 0.991 & -0.129 & 0 \\ 0.224 & 0.129 & 0.966 & 0 \\ 0 & 0 & 0 & 1 \end{bmatrix}$$

Applying equation (12) with these coefficients yields the following:

$x' = 0.974x - 0.015y - 0.224z$ $y' = -0.015x + 0.991y - 0.129z$ $z' = 0.224x + 0.129y + 0.966z$ $w' = w$

Applying equation (12) with the coefficients for the composite projection matrix yields the following:

$x'' = x'$ $y'' = y'$ $z'' = z' - 1.577w'$ $w'' = -z' + 1.577w'$

Finally, renormalizing the homogeneous coordinates by dividing through by $w''$ yields the following:

$x''' = x''/(-z'' + 1.577w'')$ $y''' = y''/(-z'' + 1.577w'')$ $z''' = -1$ $w''' = 1$

The projected two-dimensional coordinates are obtained by dropping the fourth coordinate and evaluating the remaining three-dimensional coordinates in the plane of projection, which is $z''' = -1$, yielding $(x''', y''')$.

Referring to Table (2) below, the original non-transformed three-dimensional conical polyhedron coordinates are listed in the x, y, and z columns and are identical to the coordinates listed in Table (1). The nutated coordinates are listed in the x', y', z', and w' columns. The nutated, projected coordinates are listed in the x", y", z", and w" columns. The renormalized two-dimensional coordinates are listed in the x''' and y''' columns.

TABLE (2)

| n | x | y | z | x' | y' | z' | w' | x" | y" | z" | w" | x''' | y''' |
|---|---|---|---|----|----|----|----|----|----|----|----|------|------|
| A | 0.000 | 0.000 | 0.577 | −0.129 | −0.075 | 0.558 | 1.000 | −0.129 | −0.075 | −1.020 | 1.020 | −0.127 | −0.073 |
| 0 | 1.000 | 0.000 | 0.000 | 0.974 | −0.015 | 0.224 | 1.000 | 0.974 | −0.015 | −1.353 | 1.353 | 0.720 | −0.011 |
| 1 | 0.866 | 0.500 | 0.000 | 0.837 | 0.483 | 0.259 | 1.000 | 0.837 | 0.483 | −1.319 | 1.319 | 0.634 | 0.366 |
| 2 | 0.500 | 0.866 | 0.000 | 0.474 | 0.851 | 0.224 | 1.000 | 0.474 | 0.851 | −1.353 | 1.353 | 0.351 | 0.629 |
| 3 | 0.000 | 1.000 | 0.000 | −0.015 | 0.991 | 0.129 | 1.000 | −0.015 | 0.991 | −1.448 | 1.448 | −0.010 | 0.685 |
| 4 | −0.500 | 0.866 | 0.000 | −0.500 | 0.866 | 0.000 | 1.000 | −0.500 | 0.866 | −1.577 | 1.577 | −0.317 | 0.549 |
| 5 | −0.866 | 0.500 | 0.000 | −0.851 | 0.509 | −0.129 | 1.000 | −0.851 | 0.509 | −1.707 | 1.707 | −0.499 | 0.298 |
| 6 | −1.000 | 0.000 | 0.000 | −0.974 | 0.015 | −0.224 | 1.000 | −0.974 | 0.015 | −1.801 | 1.801 | −0.541 | 0.008 |
| 7 | −0.866 | −0.500 | 0.000 | −0.837 | −0.483 | −0.259 | 1.000 | −0.837 | −0.483 | −1.836 | 1.836 | −0.456 | −0.263 |
| 8 | −0.500 | −0.866 | 0.000 | −0.474 | −0.851 | −0.224 | 1.000 | −0.474 | −0.851 | −1.801 | 1.801 | −0.263 | −0.473 |
| 9 | 0.000 | −1.000 | 0.000 | 0.015 | −0.991 | −0.129 | 1.000 | 0.015 | −0.991 | −1.707 | 1.707 | 0.009 | −0.581 |
| 10 | 0.500 | −0.866 | 0.000 | 0.500 | −0.866 | 0.000 | 1.000 | 0.500 | −0.866 | −1.577 | 1.577 | 0.317 | −0.549 |
| 11 | 0.866 | −0.500 | 0.000 | 0.851 | −0.509 | 0.129 | 1.000 | 0.851 | −0.509 | −1.448 | 1.448 | 0.588 | −0.351 |

FIG. 5 shows a nutated, projected polyhedron. The vertex numbers are noted in the figure; these correspond to the indices in the first column of Table 1 and Table 2. A grid is superimposed on the image to allow the (x, y) coordinates to be estimated. The (x, y) coordinates correspond to the x''' and y''' coordinates listed in the last two columns of Table 2.

Referring to FIG. 2B, the final step, step S216, in computing the two-dimensional representation of the nutated, projected three-dimensional geometric model is to scan-convert or rasterize the ultrasound grayscale data according to the transformed version of the three-dimensional geometric model. In one embodiment, this is accomplished by the well-understood computer graphics process of texture-mapping the grayscale data onto the nutated, projected conical polyhedron. Texture mapping was originally taught by E. Catmull in "A Subdivision Algorithm for Computer Display of Curved Surfaces," PhD Thesis, Report UTEC-CS$_c$-74-133, Computer Science Department, University of Utah, Salt Lake City, Utah, December 1974 and in "Computer Display of Curved Surfaces," Proc 1EEE, Conference on Computer Graphics, Pattern Recognition, and Data Structures, May 1975, and refined by J. F. Blinn and M. E. Newell in "Texture and Reflection in Computer Generated Images," Communications of the ACM, 19(10), October 1976, pp. 542-547, which are all hereby incorporated by reference. P. S. Heckbert in "Survey of Texture Mapping," 1EEE Computer Graphics and Applications, 6(11), November 1986, pp. 56-57, which is hereby incorporated by reference, provides a thorough survey of texture-mapping methods.

In the texture-mapping approach used in one embodiment of the invention, the vertices of the conical polyhedron may be assigned texture coordinates (u, v) in addition to their already-assigned (x, y, z) coordinates in three-dimensional space. The u and v coordinates each range from 0 to 1 with the u-coordinate representing the relative grayscale sample number and the v-coordinate representing the relative scan line number. Referring to the exemplary data table shown in FIG. 6, sample 0 corresponds to u=0 and sample SamplesPerLine-1 corresponds to u=1, while line 0 corresponds to v=0 and line LinesPerFrame-1 corresponds to v=1. Further, sample 0 with u=0 corresponds to the apex of the conical polyhedron while sample SamplesPerLine-1 with u=1 corresponds to vertices around the base. Note that the v-coordinate must take on multiple values at the apex, depending on the specific scan line being processed. In order to accommodate this, the apical vertex is duplicated into LinesPerFrame copies, each with identical (x, y, z) and u-coordinates but different v-coordinates.

Step S216 in FIG. 2B is accomplished by texture-mapping each of the transformed isosceles triangles of the conical polyhedron into (x, y) image space. For each transformed triangle, all the (x, y) image-space pixels are computed using any of a number of well-understood polygon scan-conversion algorithms. Foley et al. in "Computer Graphic Principles and Practice," Second Edition, Addison-Wesley Publishing Company, 1990, and David A. Rogers in "Procedural Elements for Computer Graphics," McGraw-Hill Book Company, 1985, which are both hereby incorporated by reference, provide descriptions of a number of polygon scan-conversion algorithms. For each pixel in each transformed triangle, the (u, v) coordinates of the texture map are computed from the (u, v) coordinates of each of the three triangle vertices. Note that if a perspective transformation is being used, linear interpolation of the (u, v) coordinates will result in distortion resulting in texture features being improperly foreshortened. Mark Feldman in "The PC Game Programminer's Encyclopedia: Texture Mapping," http://www.geocities.com/SiliconValley/2151/tmap.html, which is hereby incorporated by reference, describes several well-understood texture-mapping algorithms along with their relative accuracy (i.e. perspective correctness), speed, and implementation difficulty in Table 3, as shown below. For example, an approximate solution can be obtained via the area subdivision algorithm by decomposing each isosceles triangle in the conical polyhedron into several smaller ones, each with its own set of (x, y, z) and (u, v) vertex coordinates. An exact solution can be obtained via the "perfect" mapping algorithm by performing the perspective division while interpolating.

TABLE 3

| Technique | Accuracy | Speed | Implementation |
|---|---|---|---|
| "Perfect" Mapping | Excellent | Bad | Easy |
| Affine Mapping | Bad | Excellent | Easy |
| Area Subdivision | Ok | Poor | Ok |
| Scan line Subdivision | Excellent | Good | Ok |
| Parabolic Mapping | Poor | Good | Easy |
| Hyperbolic Mapping | Excellent | Ok | Very Difficult |
| Constant-Z Mapping | Poor | Ok | Difficult |

Once the (u, v) texture coordinates have been computed for each image-space pixel (x, y), the (u, v) coordinates are mapped to indices into the data table created by the data input unit 180. The u coordinate is mapped to a grayscale sample number and the v coordinate is mapped to a scan line number. Since u and v are nominally fractional numbers ranging from 0 to 1, a texture coordinate (u, v), when mapped to fractional grayscale sample and scan line numbers, will be bounded by four grayscale samples in the data table. In one embodiment, these four samples are linearly weighted according to their relative distance to the exact fractional sample, then summed to produce the resultant (x, y) image-space pixel value. This weighting summing technique is often referred to as bilinear interpolation.

Certain embodiments of the invention may include adding lighting and shading to enhance the visual realism of the three-dimensional geometric model. Foley et al. "Computer Graphic Principles and Practice," Second Edition, Addison-Wesley Publishing Company, 1990, which is incorporated by reference, describes several well-known lighting and shading models used in the field of computer graphics. One or more light sources is defined and placed into the object space. In addition, the reflective properties of the three-dimensional geometric model are specified. This may involve, for example, the calculation of a normal vector for each of the vertices of the conical polyhedron model or at each point on the surface of the model, as well as specifying the reflective properties such as, but not limited to, diffuse or specular reflectivity.

In one embodiment of the invention, the lighting and shading calculations are applied to the nutated axis or vertices of the three-dimensional geometric model in an additional processing step interposed between steps S212 and step S214 in FIG. 2B. These calculations produce a relative intensity value for each of the vertices in addition to the nutated coordinate values. These relative intensity values are passed through step S214 and used in step S216 to produce a final image that incorporates the effect of the lighting and shading.

In this embodiment, the light source may be placed along the positive z-axis (note that although the observer is also placed along the positive z-axis, the light source and observer will not interfere with each other). When the three-dimensional geometric model is nutated, the portion containing the most recently acquired scan lines reflects more of the incident light than the diametrically opposed, foreshortened portion because the normal vectors to the surface around the former portion are more aligned with the z-axis, i.e. the dot product of these normals with the z-axis is relatively higher. The deemphasized, foreshortened portion reflects light away from the observer because the surface normals are not well-aligned with the z-axis. Hence, it appears dimmer. The overall effect is to enhance the three-dimensional nature of the model.

The embodiments described nutate the three-dimensional geometric model in response to the manual rotation of the catheter. Additional embodiments may nutate the model at a constant or variable rate, or in response to manipulation of user interface controls. For example, in a motor-driven IVUS imaging system, where the image is being acquired repetitively several to many times per second, the model may be slowly nutated clockwise or counterclockwise, with the rate of nutation being on the order of one nutation cycle per second. Furthermore, user interface controls such as a computer pointing device may be used to interactively nutate the model. This technique allows the model to be nutated or tilted at any orientation desired by the user. The overall nutatation angle with respect to the z-axis may also be gradually or abruptly increased as new image lines are being added and gradually or abruptly decreased after a certain time period in which no new image lines were added. Referring to FIG. 2A, in these additional embodiments, the nutation matrix initialization unit 175 is modified to accept and/or generate nutation angles from sources other than the leading scan line angle. For example, for slow periodic nutation and overall nutation angle increases and decreases a timer may be used and for interactive nutation the coordinates of a computer pointing device may be used to generate and/or modulate nutation angles.

Graphics markers or icons may be superimposed on the final rasterized image. Such markers or icons may indicate, for example, the location and size of one or more auxiliary diagnostic and therapeutic devices and/or where their effects will occur. Referring to FIG. 2A, in one embodiment, the coordinates of these objects are defined in object space and transformed by the three-dimensional geometric model axis nutation unit 150 and the three-dimensional geometric model projection unit 160. Rasterization is accomplished by a process similar but not necessarily identical to that performed by the image data rasterization unit 165.

An additional embodiment allows the image to persist for a finite period of time after which it is either gradually or abruptly removed. This technique may be applied to individual scan lines within the image as well as to the entire image. One embodiment of this is to gradually fade each of the individual scan lines as more time elapses without it being updated by a fresh scan line. This has the effect that the least recently acquired or "oldest" image data becomes progressively dimmer with time while the most recently acquired or "newest" image is the brightest. This visually suggests that the older data has decreasing clinical value over time while the newest data has the greatest clinical value.

FIGS. 7A-7F are still frames taken from an exemplary display utilizing an apparatus and method according to embodiments of the invention. That is, FIGS. 7A-7F are still frames taken from a video display. The conical forward-looking image data has been rasterized onto a nutated, projected three-dimensional geometric model in the form of a nutated, projected three-dimensional conical polyhedron. The yellow line represents the leading scan line, and rotates as image data is added. The red marking represents the position of a therapeutic and/or treatment device, such as an ablation device.

The foregoing embodiments and advantages are merely exemplary and are not to be construed as limiting the invention. The present teaching can be readily applied to other types of apparatuses. The description of the invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A method of rendering for display image data from a forward-looking conical section of tissue collected by an image data collecting device, comprising:
   receiving the image data from the forward-looking conical section;
   generating a nutated projected three-dimensional geometric model of the forward-looking conical section, wherein the generating step comprises applying a nutation definition to tilt a three-dimensional geometric model corresponding to the forward-looking conical section; and
   rasterizing the image data in accordance with the nutated projected three-dimensional geometric model to produce a rasterized image for display on a graphical display.

2. The method of claim 1, further comprising:
   organizing the received image data in the form of a data table, including an angle and corresponding image data for each scan line of the image data.

3. The method of claim 1, wherein rasterizing the image data in accordance with the projected three-dimensional geometric model comprises orienting scan lines of the image data in a correct geometric perspective on a surface of the three-dimensional geometric model.

4. The method of claim 3, wherein the three-dimensional geometric model comprises a cone.

5. The method of claim 4, wherein the cone is approximated by a plurality of parametric bicubic surface patches.

6. The method of claim 5, wherein the plurality of parametric bicubic surface patches comprise at least one of Hermite surfaces, Bezier surfaces, or B-spline surfaces.

7. The method of claim 4, wherein the cone is modeled using implicit surface equations.

8. The method of claim 4, wherein the cone is modeled using explicit surface equations.

9. The method of claim 3, wherein the three-dimensional geometric model comprises a polyhedron.

10. The method of claim 9, wherein the three-dimensional geometric model comprises a conical polyhedron.

11. The method of claim 10, wherein the conical polyhedron comprises a number of triangles equivalent to a number of scan lines of the image data.

12. The method of claim 11, wherein the conical polyhedron comprises a number of triangles equivalent to a number of scan lines of the image data for a complete 360 degree rotation of the image data collection device.

13. The method of claim 11, wherein the number of triangles comprises at least 400 triangles.

14. The method of claim 10, wherein the conical polyhedron comprises a number of trapezoids equivalent to a number of scan lines of the image data such that an apex of the conical polyhedron is open.

15. The method of claim 1, wherein the nutation definition specifies an angle for nutating an axis of the three-dimensional geometric model.

16. The method of claim 15, wherein nutating the axis of the three-dimensional geometric model comprises nutating the axis of the three-dimensional geometric model at least one of a constant rate or a variable rate.

17. The method of claim 15, wherein nutating the axis of the three-dimensional geometric model comprises at least one of gradually or abruptly increasing the magnitude of nutation of the axis of the three-dimensional geometric model as scan lines of new image data are processed after a predetermined time period in which no new scan lines are added.

18. The method of claim 15, wherein nutating the axis of the three-dimensional geometric model comprises at least one of gradually or abruptly reducing the magnitude of nutation of the axis of the three-dimensional geometric model after a predetermined time period in which no new scan lines were added.

19. The method of claim 15, wherein nutating the axis of the three-dimensional geometric model comprises nutating the axis of the three-dimensional geometric model via manipulation of a user interface.

20. The method of claim 19, wherein the user interface comprises a computer pointing device.

21. The method of claim 19, wherein the user interface comprises an angle encoder.

22. The method of claim 15, wherein nutating the axis of the three-dimensional geometric model comprises nutating the axis of the three-dimensional geometric model away from scan lines corresponding to most recently acquired image data to emphasize the scan lines of the most recently acquired image data and de-emphasize via foreshortening lines diametrically opposed to the scan lines of the most recently acquired image data.

23. The method of claim 1, further comprising:
initializing a three-dimensional geometric model;
initializing a projection matrix; and
projecting the three-dimensional geometric model using the projection matrix to create the nutated projected three-dimensional geometric model.

24. The method of claim 23, further comprising:
initializing a nutation matrix; and
nutating an axis of the three-dimensional geometric model using the nutation matrix prior to projecting the three-dimensional geometric model using the projection matrix to create the nutated projected three-dimensional geometric model.

25. The method of claim 1, further comprising:
adding lighting, shading an/or texture before, during, or after rasterizing the image data.

26. The method of claim 1, further comprising:
adding markers and/or icons before, during, or after rasterizing the image data.

27. The method of claim 26, wherein the respective added markers and/or icons represent a location of one or more auxiliary diagnostic and therapeutic devices and/or where their effects will occur.

28. The method of claim 26, wherein the respective added markers and/or icons represent depth markers.

29. The method of claim 1, further comprising:
displaying the rasterized image.

30. The method of claim 29, further comprising:
displaying the rasterized image for a predetermined period of time.

31. The method of claim 30, further comprising:
at least one of gradually or abruptly removing the rasterized image after the predetermined period of time.

32. Apparatus for rendering for display image data from a forward-looking conical section of tissue collected by an image data collection device, comprising:
a data input unit configured to receive the image data from the forward-looking conical section; and
an image data processing unit including a computer-readable medium having computer-executable instructions configured to:
generate a nutated projected three-dimensional geometric model of the forward-looking conical section by applying a nutation definition to a three-dimensional geometric model, and
rasterize the image data in accordance with the nutated projected three-dimensional geometric model to produce a rasterized image for display on a graphical display.

33. The apparatus of claim 32, wherein the data input unit organizes the image data in the form of a data table, including an angle and corresponding image data for each scan line of the image data.

34. The apparatus of claim 32, wherein the image data processing unit orients scan lines of the image data in a correct geometric perspective on a surface of the three-dimensional geometric model.

35. The apparatus of claim 34, wherein the three-dimensional geometric model comprises a cone.

36. The apparatus of claim 35, wherein the cone is approximated by a plurality of parametric bicubic surface patches.

37. The apparatus of claim 36, wherein the plurality of parametric bicubic surface patches comprise at least one of Hermite surfaces, Bezier surfaces, or B-spline surfaces.

38. The apparatus of claim 35, wherein the cone is modeled using implicit surface equations.

39. The apparatus of claim 35, wherein the cone is modeled using explicit surface equations.

40. The apparatus of claim 34, wherein the three-dimensional geometric model comprises a polyhedron.

41. The apparatus of claim 40, wherein the three-dimensional model comprises a conical polyhedron.

42. The apparatus of claim 41, wherein the conical polyhedron comprises a number of triangles equivalent to a number of scan lines of the image data.

43. The apparatus of claim 42, wherein the conical polyhedron comprises a number of triangles equivalent to a number of scan lines of the image data for a complete 360 degree rotation of the image data collection device.

44. The apparatus of claim 42, wherein the number of triangles comprises at least 400 triangles.

45. The apparatus of claim 42, wherein the conical polyhedron comprises a number of trapezoids equivalent to a number of scan lines of the image data such that an apex of the conical polyhedron is open.

46. The apparatus of claim 32, wherein the image data processing unit comprises:
a three-dimensional geometric model initialization unit configured to initialize a three-dimensional geometric model;
a projection matrix initialization unit configured to initialize a projection matrix; and
a three-dimensional geometric model projection unit configured to project the three-dimensional geometric model using the projection matrix.

47. The apparatus of claim 46, wherein the image data processing unit further comprises:
a nutation matrix initialization unit configured to initialize a nutation matrix in accordance with the nutation definition; and a three-dimensional geometric model axis nutation unit configured to nutate an axis of the three-dimensional geometric model using the nutation matrix prior to projecting the three-dimensional model using the projection matrix to produce the nutated projected three-dimensional geometric model.

48. The apparatus of claim 47, further comprising:
a user manipulation device configured to control nutation of the axis of the three-dimensional geometric model.

49. The apparatus of claim 48, wherein the user manipulation device comprises a computer pointing device.

50. The apparatus of claim 48, wherein the user manipulation device comprises an angle encoder.

51. The apparatus of claim 47, wherein the image data processing unit further comprises:
an image data rasterization unit configured to rasterize the image data in accordance with the nutated projected three-dimensional geometric model.

52. The apparatus of claim 51, wherein the image data rasterization unit is further configured to add lighting, shading, and/or texture before, during, or after rasterizing the image data to enhance the appearance of three-dimensions when displayed.

53. The apparatus of claim 51, wherein the image data rasterization unit is further configured to add markers and/or icons before, during, or after rasterizing the image data.

54. An imaging system comprising the rendering apparatus of claim 32.

55. The imaging system of claim 54, wherein the imaging system comprises an IVUS system.

56. A display apparatus comprising the rendering apparatus of claim 32.

57. An imaging apparatus that scans and creates an image of a conical forward-looking section of tissue, comprising:
a transducer that is rotated in a forward-looking orientation for transmitting a signal and receiving image data resulting from interaction of the transmitted signal and tissues it encounters;
electronic circuitry that processes the received image data; and
an image data processing unit including a computer-readable medium having computer-executable instructions configured to:
generate a nutated projected three-dimensional geometric model of the forward-looking conical section by applying a nutation definition to a three-dimensional geometric model, and
rasterize the image data in accordance with the nutated projected three-dimensional geometric model to produce a rasterized image for display on a graphical display.

58. The apparatus of claim 57, wherein the three-dimensional geometric model comprises a three-dimensional cone model.

59. The imaging apparatus of claim 58, wherein the processing unit further comprises:
computer-executable instructions for adding three-dimensional lighting, shading, and/or texture visual effects to the three-dimensional cone model.

60. The imaging apparatus of claim 58, wherein the processing unit further comprises:
computer-executable instructions that facilitate nutating an axis of the three-dimensional cone model.

61. The imaging apparatus of claim 58, wherein the processing unit further comprises:
computer-executable instructions that facilitate superimposing one or more markers and/or icons on the three-dimensional cone for accurately indicating a location of one or more auxiliary diagnostic and therapeutic devices and/or where they will have effect.

62. The imaging apparatus of claim 61, wherein the processing unit further comprises computer executable instructions facilitating superimposing depth markers.

63. The imaging apparatus of claim 58, further comprising:
an interventional device, wherein the transducer is configured to image a portion of tissue while the interventional device operates on or near the tissue being imaged.

64. The imaging apparatus of claim 58, wherein the processing unit comprises computer-executable instructions facilitating persisting displaying the image data on the graphical display for a finite period of time, after which the image is either gradually or abruptly removed.

65. A method for displaying image data that has been acquired by an image data collecting device from a conical forward-looking section of tissue, comprising:
receiving the image data from the forward-looking conical section; and
displaying the image data by orienting scan lines of the image data in their correct geometric perspective on a surface of a three-dimensional geometric model, the displaying step comprising:
generating a nutated projected three-dimensional geometric model of the forward-looking conical section, wherein the generating step comprises applying a nutation definition to tilt a three-dimensional geometric model corresponding to the forward-looking conical section; and
rasterizing the image data in accordance with the nutated projected three-dimensional geometric model to produce a rasterized image for display on a graphical display.

66. The method of claim 65, wherein the three-dimensional geometric model comprises a three-dimensional cone model.

67. The method of claim 66, wherein the nutation definition specifies an angle for nutating an axis of the three-dimensional cone model.

68. The method of claim 67, further comprising:
nutating an axis of the three-dimensional cone model in real-time in response to new image scan lines being acquired during the receiving step.

69. The method of claim 67, further comprising:
nutating the axis of the three-dimensional cone away from most recently acquired scan lines so as to emphasize the most recently acquired scan lines and deemphasize, via foreshortening, lines diametrically opposed to the most recently acquired scan lines.

70. The method of claim 67, further comprising:
nutating the axis of the three-dimensional cone in real-time at least one of a constant or variable rate independent of new image lines being added.

71. The method of claim 67, further comprising:
nutating the axis of the three-dimensional cone in response to manipulation of a user interface control device.

72. The method of claim 71, where the user interface control device comprises a computer pointing device.

73. The method of claim 71, where the user interface control device comprises an angle encoder.

74. The method of claim 67, further comprising:
reducing the magnitude of the nutation angle of the three-dimensional cone model in response to no new image lines being added after a certain time period.

75. The method of claim 67, further comprising:

gradually or abruptly increasing the magnitude of nutation of the three-dimensional cone in response to new image lines being added after a certain time period in which no new image lines were added.

76. The method of claim 67, further comprising:

lighting, shading, and/or texturing the image of the three-dimensional cone in real-time as the cone nutates.

77. The method of claim 67, further comprising:

superimposing a location of one or more auxiliary diagnostic and therapeutic devices or a location of one or more actions on the image of the three-dimensional cone.

78. The method of claim 65, further comprising:

retaining the image data on the display for a predetermined period of time and thereafter removing the image data.

* * * * *